(12) United States Patent
Breton et al.

(10) Patent No.: US 12,362,838 B2
(45) Date of Patent: *Jul. 15, 2025

(54) METHOD, SYSTEM AND COMPUTER PROGRAM PRODUCT FOR REAL-TIME DETECTION OF SENSITIVITY DECLINE IN ANALYTE SENSORS

(71) Applicants: ABBOTT DIABETES CARE INC., Alameda, CA (US); UNIVERSITY OF VIRGINIA PATENT FOUNDATION, Charlottesville, VA (US)

(72) Inventors: Marc D. Breton, Charlottesville, VA (US); Boris P. Kovatchev, Charlottesville, VA (US); Erwin S. Budiman, Fremont, CA (US); Kenneth J. Doniger, Menlo Park, CA (US)

(73) Assignees: ABBOTT DIABETES CARE INC., Alameda, CA (US); UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 2 days.

This patent is subject to a terminal disclaimer.

(21) Appl. No.: 18/211,101

(22) Filed: Jun. 16, 2023

(65) Prior Publication Data
US 2024/0031039 A1 Jan. 25, 2024

Related U.S. Application Data

(63) Continuation of application No. 17/156,169, filed on Jan. 22, 2021, now Pat. No. 11,722,229, which is a (Continued)

(51) Int. Cl.
*H04B 17/00* (2015.01)
*A61B 5/00* (2006.01)
(Continued)

(52) U.S. Cl.
CPC ............. *H04B 17/00* (2013.01); *A61B 5/002* (2013.01); *A61B 5/14503* (2013.01);
(Continued)

(58) Field of Classification Search
CPC ..... H04B 17/00; A61B 5/002; A61B 5/14503; A61B 5/14532; A61B 5/14546;
(Continued)

(56) References Cited

U.S. PATENT DOCUMENTS 3,581,062 A 5/1971 Aston
3,926,760 A 12/1975 Allen et al.
(Continued)

FOREIGN PATENT DOCUMENTS

DE 4401400 7/1995
EP 0098592 1/1984
(Continued)

OTHER PUBLICATIONS

Alemzadeh, R, "Sensor-Augmented Insulin Pump Therapy: Clinical Applications", Medical College of Wisconsin Diabetes Symposium, pp. 1-61, 2011.
(Continued)

*Primary Examiner* — Tung S Lau
(74) *Attorney, Agent, or Firm* — ONE LLP

(57) ABSTRACT

Method, system and computer program product for providing real time detection of analyte sensor sensitivity decline is continuous glucose monitoring systems are provided.

15 Claims, 12 Drawing Sheets

Related U.S. Application Data continuation of application No. 15/866,384, filed on Jan. 9, 2018, now Pat. No. 10,903,914, which is a continuation of application No. 14/266,612, filed on Apr. 30, 2014, now Pat. No. 9,882,660, which is a continuation of application No. 13/418,305, filed on Mar. 12, 2012, now Pat. No. 8,718,958, which is a continuation of application No. 11/925,689, filed on Oct. 26, 2007, now Pat. No. 8,135,548.

(60) Provisional application No. 60/854,566, filed on Oct. 26, 2006.

(51) Int. Cl.
*A61B 5/145* (2006.01)
*A61B 5/1473* (2006.01)
*G16H 10/40* (2018.01)
*G16H 40/60* (2018.01)
*G16H 40/67* (2018.01)

(52) U.S. Cl.
CPC ...... *A61B 5/14532* (2013.01); *A61B 5/14546* (2013.01); *A61B 5/1473* (2013.01); *A61B 2560/0223* (2013.01); *G16H 10/40* (2018.01); *G16H 40/60* (2018.01); *G16H 40/67* (2018.01)

(58) Field of Classification Search
CPC .......... A61B 5/1473; A61B 2560/0223; G16H 10/40; G16H 40/60; G16H 40/67
See application file for complete search history.

(56) References Cited

U.S. PATENT DOCUMENTS

| | | |
|---|---|---|
| 3,949,388 A | 4/1976 | Fuller |
| 3,978,856 A | 9/1976 | Michel |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,441,968 A | 4/1984 | Emmer et al. |
| 4,462,048 A | 7/1984 | Ross |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,545,382 A | 10/1985 | Higgins et al. |
| 4,619,793 A | 10/1986 | Lee |
| 4,671,288 A | 6/1987 | Gough |
| 4,703,756 A | 11/1987 | Gough et al. |
| 4,711,245 A | 12/1987 | Higgins et al. |
| 4,731,051 A | 3/1988 | Fischell |
| 4,731,726 A | 3/1988 | Allen, III |
| 4,749,985 A | 6/1988 | Corsberg |
| 4,757,022 A | 7/1988 | Shults et al. |
| 4,759,366 A | 7/1988 | Callaghan |
| 4,777,953 A | 10/1988 | Ash et al. |
| 4,779,618 A | 10/1988 | Mund et al. |
| 4,803,638 A | 2/1989 | Nottingham et al. |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,947,845 A | 8/1990 | Davis |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,023,783 A | 6/1991 | Cohen et al. |
| 5,050,612 A | 9/1991 | Matsumura |
| 5,055,171 A | 10/1991 | Peck |
| 5,068,536 A | 11/1991 | Rosenthal |
| 5,077,476 A | 12/1991 | Rosenthal |
| 5,082,550 A | 1/1992 | Rishpon et al. |
| 5,106,365 A | 4/1992 | Hernandez |
| 5,113,869 A | 5/1992 | Nappholz et al. |
| 5,122,925 A | 6/1992 | Inpyn |
| 5,135,004 A | 8/1992 | Adams et al. |
| 5,148,812 A | 9/1992 | Verrier et al. |
| 5,165,407 A | 11/1992 | Wilson et al. |
| 5,199,428 A | 4/1993 | Obel et al. |
| 5,202,261 A | 4/1993 | Musho et al. |
| 5,203,326 A | 4/1993 | Collins |
| 5,210,778 A | 5/1993 | Massart |
| 5,231,988 A | 8/1993 | Wernicke et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,312,455 A | 5/1994 | Zadeh |
| 5,313,953 A | 5/1994 | Yomtov et al. |
| 5,320,715 A | 6/1994 | Berg |
| 5,320,725 A | 6/1994 | Gregg et al. |
| 5,322,063 A | 6/1994 | Allen et al. |
| 5,323,141 A | 6/1994 | Petek |
| 5,328,460 A | 7/1994 | Lord et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,365,426 A | 11/1994 | Siegel et al. |
| 5,372,427 A | 12/1994 | Padovani et al. |
| 5,376,070 A | 12/1994 | Purvis et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,400,795 A | 3/1995 | Murphy et al. |
| 5,408,999 A | 4/1995 | Singh et al. |
| 5,411,647 A | 5/1995 | Johnson et al. |
| 5,425,749 A | 6/1995 | Adams |
| 5,425,868 A | 6/1995 | Pedersen |
| 5,431,160 A | 7/1995 | Wilkins |
| 5,431,921 A | 7/1995 | Thombre |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,520,191 A | 5/1996 | Karlsson et al. |
| 5,531,878 A | 7/1996 | Vadgama et al. |
| 5,543,326 A | 8/1996 | Heller et al. |
| 5,552,997 A | 9/1996 | Massart |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,628,890 A | 5/1997 | Nigel et al. |
| 5,640,954 A | 6/1997 | Pfeiffer et al. |
| 5,653,239 A | 8/1997 | Pompei et al. |

(56) References Cited

U.S. PATENT DOCUMENTS

| | | |
|---|---|---|
| 5,660,163 A | 8/1997 | Schulman et al. |
| 5,665,222 A | 9/1997 | Heller et al. |
| 5,711,001 A | 1/1998 | Bussan et al. |
| 5,711,861 A | 1/1998 | Ward et al. |
| 5,720,295 A | 2/1998 | Greenhut et al. |
| 5,733,259 A | 3/1998 | Valcke et al. |
| 5,735,285 A | 4/1998 | Albert et al. |
| 5,741,211 A | 4/1998 | Renirie et al. |
| 5,772,586 A | 6/1998 | Heinonen et al. |
| 5,785,660 A | 7/1998 | van Lake et al. |
| 5,791,344 A | 8/1998 | Schulman et al. |
| 5,792,065 A | 8/1998 | Xue et al. |
| 5,820,551 A | 10/1998 | Hill et al. |
| 5,822,715 A | 10/1998 | Worthington et al. |
| 5,891,047 A | 4/1999 | Lander et al. |
| 5,899,855 A | 5/1999 | Brown |
| 5,914,026 A | 6/1999 | Blubaugh, Jr. et al. |
| 5,918,603 A | 7/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,957,854 A | 9/1999 | Besson et al. |
| 5,960,797 A | 10/1999 | Kramer et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,016,443 A | 1/2000 | Ekwall et al. |
| 6,021,350 A | 2/2000 | Mathson |
| 6,024,699 A | 2/2000 | Surwit et al. |
| 6,038,469 A | 3/2000 | Karlsson et al. |
| 6,049,727 A | 4/2000 | Crothall |
| 6,071,391 A | 6/2000 | Gotoh et al. |
| 6,073,031 A | 6/2000 | Helstab et al. |
| 6,083,710 A | 7/2000 | Heller et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,103,033 A | 8/2000 | Say et al. |
| 6,108,577 A | 8/2000 | Benser |
| 6,112,116 A | 8/2000 | Fischell |
| 6,115,628 A | 9/2000 | Stadler et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,128,526 A | 10/2000 | Stadler et al. |
| 6,134,461 A | 10/2000 | Say et al. |
| 6,143,164 A | 11/2000 | Heller et al. |
| 6,144,837 A | 11/2000 | Quy |
| 6,159,147 A | 12/2000 | Lichter et al. |
| 6,161,095 A | 12/2000 | Brown |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,233,471 B1 | 5/2001 | Berner et al. |
| 6,233,486 B1 | 5/2001 | Ekwall et al. |
| 6,248,067 B1 | 6/2001 | Causey, III et al. |
| 6,249,705 B1 | 6/2001 | Snell |
| 6,254,586 B1 | 7/2001 | Mann et al. |
| 6,256,538 B1 | 7/2001 | Ekwall |
| 6,264,606 B1 | 7/2001 | Ekwall et al. |
| 6,270,455 B1 | 8/2001 | Brown |
| 6,272,379 B1 | 8/2001 | Fischell et al. |
| 6,275,717 B1 | 8/2001 | Gross et al. |
| 6,283,761 B1 | 9/2001 | Joao |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,299,757 B1 | 10/2001 | Feldman et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,338,790 B1 | 1/2002 | Feldman et al. |
| 6,348,640 B1 | 2/2002 | Navot et al. |
| 6,359,444 B1 | 3/2002 | Grimes |
| 6,360,888 B1 | 3/2002 | McIvor et al. |
| 6,361,503 B1 | 3/2002 | Starobin et al. |
| 6,366,794 B1 | 4/2002 | Moussy et al. |
| 6,377,828 B1 | 4/2002 | Chaiken et al. |
| 6,377,852 B1 | 4/2002 | Bornzin et al. |
| 6,377,894 B1 | 4/2002 | Deweese et al. |
| 6,379,301 B1 | 4/2002 | Worthington et al. |
| 6,381,493 B1 | 4/2002 | Stadler et al. |
| 6,387,048 B1 | 5/2002 | Schulman et al. |
| 6,405,066 B1 | 6/2002 | Essenpreis et al. |
| 6,413,393 B1 | 7/2002 | Van Antwerp et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,461,496 B1 | 10/2002 | Feldman et al. |
| 6,471,689 B1 | 10/2002 | Joseph et al. |
| 6,478,736 B1 | 11/2002 | Mault |
| 6,484,046 B1 | 11/2002 | Say et al. |
| 6,501,983 B1 | 12/2002 | Natarajan et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,520,326 B2 | 2/2003 | McIvor et al. |
| 6,540,891 B1 | 4/2003 | Stewart et al. |
| 6,544,212 B2 | 4/2003 | Galley et al. |
| 6,551,494 B1 | 4/2003 | Heller et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,574,490 B2 | 6/2003 | Abbink et al. |
| 6,576,101 B1 | 6/2003 | Heller et al. |
| 6,577,899 B2 | 6/2003 | Lebel et al. |
| 6,579,690 B1 * | 6/2003 | Bonnecaze ............ A61B 5/746 435/14 |
| 6,585,644 B2 | 7/2003 | Lebel et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,616,819 B1 | 9/2003 | Liamos et al. |
| 6,618,934 B1 | 9/2003 | Feldman et al. |
| 6,622,045 B2 | 9/2003 | Snell et al. |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulson et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,720,992 B1 | 4/2004 | Zahn et al. |

(56) References Cited

U.S. PATENT DOCUMENTS

| | | |
|---|---|---|
| 6,730,200 B1 | 5/2004 | Stewart et al. |
| 6,731,985 B2 | 5/2004 | Poore et al. |
| 6,733,446 B2 | 5/2004 | Lebel et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,749,740 B2 | 6/2004 | Liamos et al. |
| 6,758,810 B2 | 7/2004 | Lebel et al. |
| 6,764,581 B1 | 7/2004 | Forrow et al. |
| 6,770,030 B1 | 8/2004 | Schaupp et al. |
| 6,773,671 B1 | 8/2004 | Lewis et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,923,763 B1 | 8/2005 | Kovatchev et al. |
| 6,931,327 B2 | 8/2005 | Goode, Jr. et al. |
| 6,932,892 B2 | 8/2005 | Chen et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman, IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,010,345 B2 | 3/2006 | Hill et al. |
| 7,016,713 B2 | 3/2006 | Gardner et al. |
| 7,016,720 B2 | 3/2006 | Kroll |
| 7,022,072 B2 | 4/2006 | Fox et al. |
| 7,024,245 B2 | 4/2006 | Lebel et al. |
| 7,025,425 B2 | 4/2006 | Kovatchev et al. |
| 7,029,443 B2 | 4/2006 | Kroll |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,287 B1 | 5/2006 | Khalil et al. |
| 7,052,483 B2 | 5/2006 | Wojcik |
| 7,056,302 B2 | 6/2006 | Douglas |
| 7,074,307 B2 | 7/2006 | Simpson et al. |
| 7,076,300 B1 | 7/2006 | Kroll et al. |
| 7,081,195 B2 | 7/2006 | Simpson et al. |
| 7,092,891 B2 | 8/2006 | Maus et al. |
| 7,096,064 B2 | 8/2006 | Deno et al. |
| 7,098,803 B2 | 8/2006 | Mann et al. |
| 7,103,412 B1 | 9/2006 | Kroll |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,134,999 B2 | 11/2006 | Brauker et al. |
| 7,136,689 B2 | 11/2006 | Shults et al. |
| 7,142,911 B2 | 11/2006 | Boileau et al. |
| 7,153,265 B2 | 12/2006 | Vachon |
| 7,167,818 B2 | 1/2007 | Brown |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,225,535 B2 | 6/2007 | Feldman et al. |
| 7,226,978 B2 | 6/2007 | Tapsak et al. |
| 7,258,673 B2 | 8/2007 | Racchini et al. |
| 7,267,665 B2 | 9/2007 | Steil et al. |
| 7,272,436 B2 | 9/2007 | Gill et al. |
| 7,276,029 B2 | 10/2007 | Goode, Jr. et al. |
| 7,278,983 B2 | 10/2007 | Ireland et al. |
| 7,295,867 B2 | 11/2007 | Berner et al. |
| 7,297,114 B2 | 11/2007 | Gill et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,402,153 B2 | 7/2008 | Steil et al. |
| 7,404,796 B2 | 7/2008 | Ginsberg |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,474,992 B2 | 1/2009 | Ariyur |
| 7,494,465 B2 | 2/2009 | Brister et al. |
| 7,497,827 B2 | 3/2009 | Brister et al. |
| 7,499,002 B2 | 3/2009 | Blasko et al. |
| 7,502,644 B2 | 3/2009 | Gill et al. |
| 7,519,408 B2 | 4/2009 | Rasdal et al. |
| 7,524,287 B2 | 4/2009 | Bharmi |
| 7,547,281 B2 | 6/2009 | Hayes et al. |
| 7,569,030 B2 | 8/2009 | Lebel et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,649,805 B2 | 1/2010 | Bose et al. |
| 7,699,775 B2 | 4/2010 | Desai et al. |
| 7,699,964 B2 | 4/2010 | Feldman et al. |
| 7,736,310 B2 | 6/2010 | Taub et al. |
| 7,766,829 B2 | 8/2010 | Sloan et al. |
| 7,771,352 B2 | 8/2010 | Shults et al. |
| 7,774,145 B2 | 8/2010 | Brauker et al. |
| 7,778,680 B2 | 8/2010 | Goode, Jr. et al. |
| 7,826,981 B2 | 11/2010 | Goode, Jr. et al. |
| 7,866,026 B1 | 1/2011 | Wang et al. |
| 7,885,698 B2 | 2/2011 | Feldman |
| 7,889,069 B2 | 2/2011 | Fifolt et al. |
| 7,899,511 B2 | 3/2011 | Shults et al. |
| 7,905,833 B2 | 3/2011 | Brister et al. |
| 7,914,450 B2 | 3/2011 | Goode, Jr. et al. |
| 7,922,665 B2 | 4/2011 | Baker, Jr. |
| 7,938,797 B2 | 5/2011 | Estes |
| 7,974,672 B2 | 7/2011 | Shults et al. |
| 8,282,549 B2 | 10/2012 | Brauker et al. |
| 9,885,674 B2 | 2/2018 | Ouvrier-Buffet et al. |
| 10,903,914 B2* | 1/2021 | Breton ............... A61B 5/14532 |
| 2001/0041831 A1 | 11/2001 | Starkweather et al. |
| 2002/0019022 A1 | 2/2002 | Dunn et al. |
| 2002/0042090 A1 | 4/2002 | Heller et al. |
| 2002/0068860 A1 | 6/2002 | Clark |
| 2002/0103499 A1 | 8/2002 | Perez et al. |
| 2002/0106709 A1 | 8/2002 | Potts et al. |
| 2002/0128594 A1 | 9/2002 | Das et al. |
| 2002/0143266 A1 | 10/2002 | Bock |
| 2002/0143372 A1 | 10/2002 | Snell et al. |
| 2002/0161288 A1 | 10/2002 | Shin et al. |
| 2002/0169635 A1 | 11/2002 | Shillingburg |

(56) References Cited

U.S. PATENT DOCUMENTS

| | | |
|---|---|---|
| 2002/0193679 A1 | 12/2002 | Malave et al. |
| 2003/0000522 A1 | 1/2003 | Lynn et al. |
| 2003/0004403 A1 | 1/2003 | Drinan et al. |
| 2003/0023317 A1 | 1/2003 | Brauker et al. |
| 2003/0023461 A1 | 1/2003 | Quintanilla et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0050546 A1 | 3/2003 | Desai et al. |
| 2003/0052663 A1 | 3/2003 | Frauscher |
| 2003/0065308 A1 | 4/2003 | Lebel et al. |
| 2003/0100821 A1 | 5/2003 | Heller et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0019275 A1 | 1/2004 | Iatrou et al. |
| 2004/0024553 A1 | 2/2004 | Monfre et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0064068 A1 | 4/2004 | DeNuzzio et al. |
| 2004/0077962 A1 | 4/2004 | Kroll |
| 2004/0078065 A1 | 4/2004 | Kroll |
| 2004/0099529 A1 | 5/2004 | Mao et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0135684 A1 | 7/2004 | Steinthal et al. |
| 2004/0138588 A1 | 7/2004 | Saikley et al. |
| 2004/0138716 A1 | 7/2004 | Kon et al. |
| 2004/0146909 A1 | 7/2004 | Duong et al. |
| 2004/0152622 A1 | 8/2004 | Keith et al. |
| 2004/0167801 A1 | 8/2004 | Say et al. |
| 2004/0171921 A1 | 9/2004 | Say et al. |
| 2004/0172307 A1 | 9/2004 | Gruber |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204687 A1 | 10/2004 | Mogensen et al. |
| 2004/0208780 A1 | 10/2004 | Faries, Jr. et al. |
| 2004/0225338 A1 | 11/2004 | Lebel et al. |
| 2004/0236200 A1 | 11/2004 | Say et al. |
| 2004/0249253 A1 | 12/2004 | Racchini et al. |
| 2004/0249420 A1 | 12/2004 | Olson et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0263354 A1 | 12/2004 | Mann et al. |
| 2004/0267300 A1 | 12/2004 | Mace |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0010087 A1 | 1/2005 | Banet et al. |
| 2005/0010269 A1 | 1/2005 | Lebel et al. |
| 2005/0016276 A1 | 1/2005 | Guan et al. |
| 2005/0017864 A1 | 1/2005 | Tsoukalis |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0049179 A1 | 3/2005 | Davidson et al. |
| 2005/0070774 A1 | 3/2005 | Addison et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0112169 A1 | 5/2005 | Brauker et al. |
| 2005/0113653 A1 | 5/2005 | Fox et al. |
| 2005/0114068 A1 | 5/2005 | Chey et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0154271 A1 | 7/2005 | Rasdal et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0214892 A1 | 9/2005 | Kovatchev et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0277164 A1 | 12/2005 | Drucker et al. |
| 2005/0277912 A1 | 12/2005 | John |
| 2005/0287620 A1 | 12/2005 | Heller et al. |
| 2005/0288725 A1 | 12/2005 | Hettrick et al. |
| 2006/0001538 A1 | 1/2006 | Kraft et al. |
| 2006/0004270 A1 | 1/2006 | Bedard et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025662 A1 | 2/2006 | Buse et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0058588 A1 | 3/2006 | Zdeblick |
| 2006/0088940 A1* | 4/2006 | Feingold .......... G01N 35/00732 422/67 |
| 2006/0091006 A1 | 5/2006 | Wang et al. |
| 2006/0142651 A1 | 6/2006 | Brister et al. |
| 2006/0155180 A1 | 7/2006 | Brister et al. |
| 2006/0166629 A1 | 7/2006 | Reggiardo |
| 2006/0167365 A1 | 7/2006 | Bharmi |
| 2006/0167517 A1 | 7/2006 | Gill et al. |
| 2006/0167518 A1 | 7/2006 | Gill et al. |
| 2006/0167519 A1 | 7/2006 | Gill et al. |
| 2006/0173260 A1 | 8/2006 | Gaoni et al. |
| 2006/0173406 A1 | 8/2006 | Hayes et al. |

(56) References Cited

U.S. PATENT DOCUMENTS

| | | |
|---|---|---|
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189863 A1 | 8/2006 | Peyser et al. |
| 2006/0193375 A1 | 8/2006 | Lee |
| 2006/0195041 A1 | 8/2006 | Lynn et al. |
| 2006/0222566 A1 | 10/2006 | Brauker et al. |
| 2006/0224109 A1 | 10/2006 | Steil et al. |
| 2006/0226985 A1 | 10/2006 | Goodnow et al. |
| 2006/0229512 A1 | 10/2006 | Petisce et al. |
| 2006/0247508 A1 | 11/2006 | Fennell |
| 2006/0247685 A1 | 11/2006 | Bharmi |
| 2006/0247985 A1 | 11/2006 | Liamos et al. |
| 2006/0258929 A1 | 11/2006 | Goode et al. |
| 2006/0264785 A1 | 11/2006 | Dring et al. |
| 2006/0272652 A1 | 12/2006 | Stocker et al. |
| 2006/0281985 A1 | 12/2006 | Ward et al. |
| 2007/0016381 A1 | 1/2007 | Kamath et al. |
| 2007/0027381 A1 | 2/2007 | Stafford |
| 2007/0032706 A1 | 2/2007 | Kamath et al. |
| 2007/0033074 A1 | 2/2007 | Nitzan et al. |
| 2007/0038044 A1 | 2/2007 | Dobbles et al. |
| 2007/0056858 A1 | 3/2007 | Chen et al. |
| 2007/0060803 A1 | 3/2007 | Liljeryd et al. |
| 2007/0060814 A1 | 3/2007 | Stafford |
| 2007/0066873 A1 | 3/2007 | Kamath et al. |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0095661 A1 | 5/2007 | Wang et al. |
| 2007/0106135 A1 | 5/2007 | Sloan et al. |
| 2007/0108048 A1 | 5/2007 | Wang et al. |
| 2007/0118405 A1 | 5/2007 | Campbell et al. |
| 2007/0124002 A1 | 5/2007 | Estes et al. |
| 2007/0129647 A1 | 6/2007 | Lynn |
| 2007/0149875 A1 | 6/2007 | Ouyang et al. |
| 2007/0156033 A1 | 7/2007 | Causey, III et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179434 A1 | 8/2007 | Weinert et al. |
| 2007/0191701 A1 | 8/2007 | Feldman et al. |
| 2007/0199818 A1 | 8/2007 | Petyt et al. |
| 2007/0203407 A1 | 8/2007 | Hoss et al. |
| 2007/0203966 A1 | 8/2007 | Brauker et al. |
| 2007/0213657 A1 | 9/2007 | Jennewine et al. |
| 2007/0227911 A1 | 10/2007 | Wang et al. |
| 2007/0232877 A1 | 10/2007 | He |
| 2007/0232878 A1 | 10/2007 | Kovatchev et al. |
| 2007/0232880 A1 | 10/2007 | Siddiqui et al. |
| 2007/0233013 A1 | 10/2007 | Schoenberg et al. |
| 2007/0235331 A1 | 10/2007 | Simpson et al. |
| 2007/0249922 A1 | 10/2007 | Peyser et al. |
| 2007/0255321 A1 | 11/2007 | Gerber et al. |
| 2007/0282299 A1 | 12/2007 | Hellwig |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0017522 A1 | 1/2008 | Heller et al. |
| 2008/0021666 A1 | 1/2008 | Goode, Jr. et al. |
| 2008/0029391 A1 | 2/2008 | Mao et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0064937 A1 | 3/2008 | McGarraugh et al. |
| 2008/0066305 A1 | 3/2008 | Wang et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097289 A1 | 4/2008 | Steil et al. |
| 2008/0102441 A1 | 5/2008 | Chen et al. |
| 2008/0108942 A1 | 5/2008 | Brister et al. |
| 2008/0119703 A1 | 5/2008 | Brister et al. |
| 2008/0119708 A1 | 5/2008 | Budiman |
| 2008/0139910 A1 | 6/2008 | Mastrototaro et al. |
| 2008/0148873 A1 | 6/2008 | Wang |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0172205 A1 | 7/2008 | Breton et al. |
| 2008/0177149 A1 | 7/2008 | Weinert et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0208113 A1 | 8/2008 | Damiano et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0234943 A1 | 9/2008 | Ray et al. |
| 2008/0242961 A1 | 10/2008 | Brister et al. |
| 2008/0242963 A1 | 10/2008 | Essenpreis et al. |
| 2008/0255434 A1 | 10/2008 | Hayter et al. |
| 2008/0255437 A1 | 10/2008 | Hayter |
| 2008/0255808 A1 | 10/2008 | Hayter |
| 2008/0256048 A1 | 10/2008 | Hayter |
| 2008/0262469 A1 | 10/2008 | Brister et al. |
| 2008/0267823 A1 | 10/2008 | Wang et al. |
| 2008/0275313 A1 | 11/2008 | Brister et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2008/0319279 A1 | 12/2008 | Ramsay et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |

(56) References Cited

U.S. PATENT DOCUMENTS

| | | |
|---|---|---|
| 2009/0006061 A1 | 1/2009 | Thukral et al. |
| 2009/0006133 A1 | 1/2009 | Weinert et al. |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054748 A1 | 2/2009 | Feldman et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0099436 A1 | 4/2009 | Brister et al. |
| 2009/0105560 A1 | 4/2009 | Solomon |
| 2009/0105570 A1 | 4/2009 | Sloan et al. |
| 2009/0105636 A1 | 4/2009 | Hayter et al. |
| 2009/0112478 A1 | 4/2009 | Mueller, Jr. et al. |
| 2009/0118589 A1 | 5/2009 | Ueshima et al. |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0252196 A1 | 10/2009 | Icove et al. |
| 2009/0253973 A1 | 10/2009 | Bashan et al. |
| 2009/0257536 A1 | 10/2009 | Grbic et al. |
| 2009/0287073 A1 | 11/2009 | Boock et al. |
| 2009/0287074 A1 | 11/2009 | Shults et al. |
| 2009/0294277 A1 | 12/2009 | Thomas et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063372 A1 | 3/2010 | Potts et al. |
| 2010/0081909 A1 | 4/2010 | Budiman et al. |
| 2010/0085573 A1 | 4/2010 | Lu et al. |
| 2010/0094112 A1* | 4/2010 | Heller ............... A61B 5/14865 600/345 |
| 2010/0121167 A1 | 5/2010 | McGarraugh et al. |
| 2010/0141656 A1 | 6/2010 | Krieftewirth |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174266 A1 | 7/2010 | Estes |
| 2010/0191085 A1 | 7/2010 | Budiman |
| 2010/0198034 A1 | 8/2010 | Thomas et al. |
| 2010/0198142 A1 | 8/2010 | Sloan et al. |
| 2010/0213057 A1 | 8/2010 | Feldman et al. |
| 2010/0230285 A1 | 9/2010 | Hoss et al. |
| 2010/0234710 A1 | 9/2010 | Budiman et al. |
| 2010/0280441 A1 | 11/2010 | Willinska et al. |
| 2010/0312176 A1 | 12/2010 | Lauer et al. |
| 2010/0313105 A1 | 12/2010 | Nekoomaram et al. |
| 2010/0317952 A1 | 12/2010 | Budiman et al. |
| 2010/0324392 A1 | 12/2010 | Yee et al. |
| 2010/0326842 A1 | 12/2010 | Mazza et al. |
| 2011/0021889 A1 | 1/2011 | Hoss et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0077490 A1 | 3/2011 | Simpson et al. |
| 2011/0077494 A1 | 3/2011 | Doniger et al. |
| 2011/0082484 A1 | 4/2011 | Saravia et al. |
| 2011/0106126 A1 | 5/2011 | Love et al. |
| 2011/0148905 A1 | 6/2011 | Simmons et al. |
| 2011/0190603 A1 | 8/2011 | Stafford |
| 2011/0191044 A1 | 8/2011 | Stafford |
| 2011/0208027 A1 | 8/2011 | Wagner et al. |
| 2011/0208155 A1 | 8/2011 | Palerm et al. |
| 2011/0213225 A1 | 9/2011 | Bernstein et al. |
| 2011/0224523 A1 | 9/2011 | Budiman |
| 2011/0257495 A1 | 10/2011 | Hoss et al. |
| 2011/0257895 A1 | 10/2011 | Brauker et al. |
| 2011/0263958 A1 | 10/2011 | Brauker et al. |
| 2011/0288574 A1 | 11/2011 | Curry et al. |
| 2011/0319729 A1 | 12/2011 | Donnay et al. |
| 2011/0320130 A1 | 12/2011 | Valdes et al. |
| 2012/0010642 A1 | 1/2012 | Lee et al. |
| 2012/0078071 A1 | 3/2012 | Bohm et al. |
| 2012/0108934 A1 | 5/2012 | Valdes et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2013/0035575 A1 | 2/2013 | Mayou et al. |
| 2013/0184547 A1 | 7/2013 | Taub et al. |
| 2014/0073871 A1 | 3/2014 | Rodriguez-Llorente et al. |
| 2014/0121480 A1 | 5/2014 | Budiman et al. |
| 2014/0131583 A1 | 5/2014 | Giarmana |
| 2016/0066828 A1* | 3/2016 | Phan ............... A61B 5/1455 600/362 |

(56) References Cited

U.S. PATENT DOCUMENTS

| | | |
|---|---|---|
| 2016/0109591 A1 | 4/2016 | Kamil Amin et al. |
| 2017/0108358 A1 | 4/2017 | Bastianini |
| 2018/0136359 A1 | 5/2018 | Wilt et al. |

FOREIGN PATENT DOCUMENTS

| | | |
|---|---|---|
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0472411 | 2/1992 |
| EP | 0286118 | 1/1995 |
| EP | 0867146 | 9/1998 |
| EP | 1048264 | 11/2000 |
| EP | 1419731 | 5/2004 |
| EP | 0939602 | 9/2004 |
| EP | 1850909 | 4/2010 |
| EP | 1677668 | 7/2010 |
| GB | 2409951 | 7/2005 |
| JP | 2002-513602 | 5/2002 |
| JP | 2004-358261 | 12/2004 |
| WO | WO-1996/025089 | 8/1996 |
| WO | WO-1996/035370 | 11/1996 |
| WO | WO-1997/015227 | 5/1997 |
| WO | WO-1998/035053 | 8/1998 |
| WO | WO-1999/056613 | 11/1999 |
| WO | WO-2000/049940 | 8/2000 |
| WO | WO-2000/059370 | 10/2000 |
| WO | WO-2000/074753 | 12/2000 |
| WO | WO-2000/078992 | 12/2000 |
| WO | WO-2001/052935 | 7/2001 |
| WO | WO-2001/054753 | 8/2001 |
| WO | WO-2002/016905 | 2/2002 |
| WO | WO-2002/058537 | 8/2002 |
| WO | WO-2003/076893 | 9/2003 |
| WO | WO-2003/082091 | 10/2003 |
| WO | WO-2003/085372 | 10/2003 |
| WO | WO-2004/060455 | 7/2004 |
| WO | WO-2004/061420 | 7/2004 |
| WO | WO-2005/041766 | 5/2005 |
| WO | WO-2005/065542 | 7/2005 |
| WO | WO-2005/089103 | 9/2005 |
| WO | WO-2006/024671 | 3/2006 |
| WO | WO-2006/079114 | 7/2006 |
| WO | WO-2006/081336 | 8/2006 |
| WO | WO-2006/086423 | 8/2006 |
| WO | WO-2006/118947 | 11/2006 |
| WO | WO-2007/016399 | 2/2007 |
| WO | WO-2007/027788 | 3/2007 |
| WO | WO-2007/041069 | 4/2007 |
| WO | WO-2007/041070 | 4/2007 |
| WO | WO-2007/041072 | 4/2007 |
| WO | WO-2007/041248 | 4/2007 |
| WO | WO-2007/056638 | 5/2007 |
| WO | WO-2007/101223 | 9/2007 |
| WO | WO-2007/115094 | 10/2007 |
| WO | WO-2007/120363 | 10/2007 |
| WO | WO-2007/126444 | 11/2007 |
| WO | WO-2007/053832 | 12/2007 |
| WO | WO-2007/143225 | 12/2007 |
| WO | WO-2008/001366 | 1/2008 |
| WO | WO-2008/021913 | 2/2008 |
| WO | WO-2008/042760 | 4/2008 |
| WO | WO-2008/052057 | 5/2008 |
| WO | WO-2008/086541 | 7/2008 |
| WO | WO-2008/128210 | 10/2008 |
| WO | WO-2008/130896 | 10/2008 |
| WO | WO-2008/130897 | 10/2008 |
| WO | WO-2008/130898 | 10/2008 |
| WO | WO-2008/143943 | 11/2008 |
| WO | WO-2009/018058 | 2/2009 |
| WO | WO-2009/086216 | 7/2009 |
| WO | WO-2009/096992 | 8/2009 |
| WO | WO-2009/097594 | 8/2009 |
| WO | WO-2012/107801 | 8/2012 |

OTHER PUBLICATIONS

Armour, J. C., et al., "Application of Chronic Intravascular Blood Glucose Sensor in Dogs", Diabetes, vol. 39, 1990, pp. 1519-1526.

Bennion, N., et al., "Alternate Site Glucose Testing: A Crossover Design", Diabetes Technology & Therapeutics, vol. 4, No. 1, 2002, pp. 25-33.

Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, vol. 4624, 2002, pp. 1-10.

Blendea, M. C., et al., "Heart Disease in Diabetic Patients", Current Diabetes Reports, vol. 3, 2003, pp. 223-229.

Bremer, T. M., et al., "Benchmark Data from the Literature for Evaluation of New Glucose Sensing Technologies", Diabetes Technology & Therapeutics, vol. 3, No. 3, 2001, pp. 409-418.

Brooks, S. L., et al., "Development of an On-Line Glucose Sensor for Fermentation Monitoring", Biosensors, vol. 3, 1987/88, pp. 45-56.

Cass, A. E., et al., "Ferrocene-Medicated Enzyme Electrode for Amperometric Determination of Glucose", Analytical Chemistry, vol. 56, No. 4, 1984, 667-671.

Cheyne, E. H., et al., "Performance of a Continuous Glucose Monitoring System During Controlled Hypoglycaemia in Healthy Volunteers", Diabetes Technology & Therapeutics, vol. 4, No. 5, 2002, pp. 607-613.

Choleau, C., et al., "Calibration of a Subcutaneous Amperometric Glucose Sensor Implanted for 7 Days in Diabetic Patients Part 2. Superiority of the One-Point Calibration Method", Biosensors and Bioelectronics, vol. 17, No. 8, 2002, pp. 647-654.

Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.

Diabetes Control and Complications Trial Research Group, "The Effect of Intensive Treatment of Diabetes on the Development and Progression of Long-Term Complications in Insulin-Dependent Diabetes Mellitus", New England J. Med. vol. 329, 1993, pp. 977-986.

Eckert, B. et al. "Hypoglycaemia Leads to an Increased QT Interval in Normal Men", Clinical Physiology, vol. 18, No. 6, 1998, pp. 570-575.

Feldman, B., et al., "A Continuous Glucose Sensor Based on Wired Enzyme™ Technology—Results from a 3-Day Trial in Patients with Type 1 Diabetes", Diabetes Technology & Therapeutics, vol. 5, No. 5, 2003, pp. 769-779.

Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.

Georgescu, B., et al., "Real-Time Multimodel Tracking of Myocardium in Echocardiography Using Robust Information Fusion", Medical Image Computing and Computer-Assisted Intervention, 2004, pp. 777-785.

Goldman, J. M., et al., "Masimo Signal Extraction Pulse Oximetry", Journal of Clinical Monitoring and Computing, vol. 16, No. 7, 2000, pp. 475-483.

Guerci, B., et al., "Clinical Performance of CGMS in Type 1 Diabetic Patients Treated by Continuous Subcutaneous Insulin Infusion Using Insulin Analogs", Diabetes Care, vol. 26, 2003, pp. 582-589.

Harris, N.D., et al., "Can Changes in QT Interval be Used to Predict the Onset of Hypoglycemia in Type 1 Diabetes?", Computers in Cardiology, vol. 27, 2000, pp. 375-378.

Heller, S. R., "Abnormalities of the Electrocardiogram During Hypoglycemia: The Cause of the Dead in Bed Syndrome?" International Journal of Clinical Practice, Suppl. No. 129, 2002, pp. 27-32.

(56) References Cited

OTHER PUBLICATIONS

Isermann, R., "Supervision, Fault-Detection and Fault-Diagnosis Methods—An Introduction", Control Engineering Practice, vol. 5, No. 5, 1997, pp. 639-652.

Isermann, R., et al., "Trends in the Application of Model-Based Fault Detection and Diagnosis of Technical Processes", Control Engineering Practice, vol. 5, No. 5, 1997, pp. 709-719.

Johnson, P. C., "Peripheral Circulation", John Wiley & Sons, 1978, pp. 198.

Jones, T. W., et al., "Mild Hypoglycemia and Impairment of Brain Stem and Cortical Evoked Potentials in Healthy Subjects", Diabetes vol. 39, 1990, 1550-1555.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", Diabetes Care, vol. 24, No. 7, 2001, pp. 1303-1304.

Kaplan, S. M., "Wiley Electrical and Electronics Engineering Dictionary", IEEE Press, 2004, pp. 141, 142, 548, 549.

Kovatchev, B. P., et al., "Evaluating the Accuracy of Continuous Glucose-Monitoring Sensors", Diabetes Care, vol. 27, No. 8, 2004, pp. 1922-1928.

Kuure-Kinsey, M., et al., "A Dual-Rate Kalman Filter for Continuous Glucose Monitoring", Proceedings of the 28th IEEE, EMBS Annual International Conference, New York City, 2006, pp. 63-66.

Landstedt-Hallin, L., et al., "Increased QT Dispersion During Hypoglycaemia in Patients with Type 2 Diabetes Mellitus", Journal of Internal Medicine, vol. 246, 1999, 299-307.

Lodwig, V., et al., "Continuous Glucose Monitoring with Glucose Sensors: Calibration and Assessment Criteria", Diabetes Technology & Therapeutics, vol. 5, No. 4, 2003, pp. 573-587.

Lortz, J., et al., "What is Bluetooth? We Explain the Newest Short-Range Connectivity Technology", Smart Computing Learning Series, Wireless Computing, vol. 8, Issue 5, 2002, pp. 72-74.

Maher, "A Method for Extrapolation of Missing Digital Audio Data", Preprints of Papers Presented at the AES Convention, 1993, pp. 1-19.

Maher, "Audio Enhancement using Nonlinear Time-Frequency Filtering", AES 26th International Conference, 2005, pp. 1-9.

Malin, S. F., et al., "Noninvasive Prediction of Glucose by Near-Infrared Diffuse Reflectance Spectoscopy", Clinical Chemistry, vol. 45, No. 9, 1999, pp. 1651-1658.

Malmberg, K., "Prospective Randomised Study of Intensive Insulin Treatment on Long-Term Survival After Acute Myocardial Infarction in Patients with Diabetes Mellitus", British Medical Journal, vol. 314, 1997, pp. 1512-1515.

Markel, A. et al., "Hypoglycaemia-Induced Ischaemic ECG Changes", Presse Medicale, vol. 23, No. 2, 1994, pp. 78-79.

McGarraugh, G., et al., "Glucose Measurements Using Blood Extracted from the Forearm and the Finger", TheraSense, Inc., 2001, 16 Pages.

McGarraugh, G., et al., "Physiological Influences on Off-Finger Glucose Testing", Diabetes Technology & Therapeutics, vol. 3, No. 3, 2001, pp. 367-376.

McKean, B. D., et al., "A Telemetry-Instrumentation System for Chronically Implanted Glucose and Oxygen Sensors", IEEE Transactions on Biomedical Engineering, vol. 35, No. 7, 1988, pp. 526-532.

Morbiducci, U, et al., "Improved Usability of the Minimal Model of Insulin Sensitivity Based on an Automated Approach and Genetic Algorithms for Parameter Estimation", Clinical Science, vol. 112, 2007, pp. 257-263.

Mougiakakou, et al., "A Real Time Simulation Model of Glucose-Insulin Metabolism for Type 1 Diabetes Patients", Proceedings of the 2005 IEEE, 2005, pp. 298-301.

Okin, P. M., et al., "Electrocardiographic Repolarization Complexity and Abnormality Predict All-Cause and Cardiovascular Mortality in Diabetes", Diabetes, vol. 53, 2004, pp. 434-440.

Panteleon, A. E., et al., "The Role of the Independent Variable to Glucose Sensor Calibration", Diabetes Technology & Therapeutics, vol. 5, No. 3, 2003, pp. 401-410.

Parker, R., et al., "Robust H∞ Glucose Control in Diabetes Using a Physiological Model", AIChE Journal, vol. 46, No. 12, 2000, pp. 2537-2549.

Peterson, K., et al., "Regulation of Serum Potassium During Insulin-Induced Hypoglycemia", Diabetes, vol. 31, 1982, pp. 615-617.

Pickup, J., et al., "Implantable Glucose Sensors: Choosing the Appropriate Sensing Strategy", Biosensors, vol. 3, 1987/88, pp. 335-346.

Pickup, J., et al., "In Vivo Molecular Sensing in Diabetes Mellitus: An Implantable Glucose Sensor with Direct Electron Transfer", Diabetologia, vol. 32, 1989, pp. 213-217.

Pishko, M. V., et al., "Amperometric Glucose Microelectrodes Prepared Through Immobilization of Glucose Oxidase in Redox Hydrogels", Analytical Chemistry, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", The American Physiological Society, 1995, E155-E161.

Rana, B. S., et al., "Relation of QT Interval Dispersion to the Number of Different Cardiac Abnormalities in Diabetes Mellitus", The American Journal of Cardiology, vol. 90, 2002, pp. 483-487.

Robinson, R. T. C. E., et al. "Changes in Cardiac Repolarization During Clinical Episodes of Nocturnal Hypoglycaemia in Adults with Type 1 Diabetes", Diabetologia, vol. 47, 2004, pp. 312-315.

Roe, J. N., et al., "Bloodless Glucose Measurements", Critical Review in Therapeutic Drug Carrier Systems, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", Artificial Organs Today, vol. 2, No. 2, 1992, pp. 145-158.

Sakakida, M., et al., "Ferrocene-Mediated Needle-Type Glucose Sensor Covered with Newly Designed Biocompatible Membrane", Sensors and Actuators B, vol. 13-14, 1993, pp. 319-322.

Salehi, C., et al., "A Telemetry-Instrumentation System for Long-Term Implantable Glucose and Oxygen Sensors", Analytical Letters, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.

Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401-406.

Shichiri, M., et al., "Glycaemic Control in Pancreatectomized Dogs with a Wearable Artificial Endocrine Pancreas", Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers", Hormone and Metabolic Research Supplement Series, vol. 20, 1988, pp. 17-20.

Shichiri, M., et al., "Membrane Design for Extending the Long-Life of an Implantable Glucose Sensor", Diabetes Nutrition and Metabolism, vol. 2, 1989, pp. 309-313.

Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", Diabetes Care, vol. 9, No. 3, 1986, pp. 298-301.

Shichiri, M., et al., "Wearable Artificial Endocrine Pancreas With Needle-Type Glucose Sensor", The Lancet, 1982, pp. 1129-1131.

Shults, M. C., et al., "A Telemetry-Instrumentation System for Monitoring Multiple Subcutaneously Implanted Glucose Sensors", IEEE Transactions on Biomedical Engineering, vol. 41, No. 10, 1994, pp. 937-942.

(56) References Cited

OTHER PUBLICATIONS

Steinhaus, B. M., et al., "The Information Content of the Cardiac Electrogram at the Stimulus Site", Annual International Conference of the IEEE Engineering in Medicine and Biology Society, vol. 12, No. 2, 1990, 0607-0609.
Sternberg, R., et al., "Study and Development of Multilayer Needle-Type Enzyme-Based Glucose Microsensors", Biosensors, vol. 4, 1988, pp. 27-40.
Thompson, M., et al., "In Vivo Probes: Problems and Perspectives", Clinical Biochemistry, vol. 19, 1986, pp. 255-261.
Turner, A., et al., "Diabetes Mellitus: Biosensors for Research and Management", Biosensors, vol. 1, 1985, pp. 85-115.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", Biosensors in the Body: Continuous in vivo Monitoring, Chapter 4, 1997, pp. 117-137.
Velho, G., et al., "Strategies for Calibrating a Subcutaneous Glucose Sensor", Biomedica Biochimica Acta, vol. 48, 1989, pp. 957-964.
Whipple, G., "Low Residual Noise Speech Enhancement Utilizing Time-Frequency", Proceedings of the International Conference on Acoustics, Speech, and Signal Processing, vol. 19, 1994, pp. 15-18.
Wilson, G. S., et al., "Progress Toward the Development of an Implantable Sensor for Glucose", Clinical Chemistry, vol. 38, No. 9, 1992, pp. 1613-1617.
Wolfe, P. J., et al., "Interpolation of Missing Data Values for Audio Signal Restoration Using a Gabor Regression Model", 2005 IEEE International Conference on Acoustics, Speech, and Signal Processing, vol. 5, 2005, pp. 517-520.
Canadian Patent Application No. 2,620,586, Examiner's Report mailed Jan. 17, 2013.
Canadian Patent Application No. 2,620,586, Examiner's Report mailed Jun. 13, 2012.
Canadian Patent Application No. 2,667,930, Examiner's Report mailed Mar. 2, 2010.
Canadian Patent Application No. 2,667,930, Notice of Allowance mailed Oct. 14, 2010.
Chinese Patent Application No. 20068004174.4, Original Language and English Translation of Notification of Granting a Patent Right for an Invention mailed Jun. 27, 2011.
Chinese Patent Application No. 20068004174.4, Original Language and English Translation of Office Action mailed Feb. 5, 2010.
Chinese Patent Application No. 20068004174.4, Original Language and English Translation of Office Action mailed Mar. 16, 2011.
Chinese Patent Application No. 20068004174.4, Original Language and English Translation of Office Action mailed Oct. 11, 2010.
Chinese Patent Application No. 200780048289.2, Original Language and English Translation of First Office Action mailed Oct. 13, 2010.
Chinese Patent Application No. 200780048289.2, Original Language and English Translation of Office Action mailed Jul. 6, 2011.
European Patent Application No. 06790080.3, Extended European Search Report mailed Feb. 8, 2010.
European Patent Application No. 07844653.1, Extended European Search Report mailed Mar. 2, 2011.
European Patent Application No. 07854382.4, Extended European Search Report mailed Dec. 23, 2009.
Japanese Patent Application No. 2008-529194, Original Language and English Translation of Office Action mailed Dec. 20, 2011.
Japanese Patent Application No. 2008-529194, Original Language and English Translation of Office Action mailed Nov. 26, 2013.
Japanese Patent Application No. 2008-529194, Original Language and English Translation of Office Action mailed Nov. 6, 2012.
Japanese Patent Application No. 2009-534910, Original Language and English Translation of Office Action mailed Aug. 2, 2011.
Japanese Patent Application No. 2012-138495, Original Language and English Translation of Office Action mailed Nov. 26, 2013.
PCT Application No. PCT/US2006/033724, International Preliminary Report on Patentability and Written Opinion of the International Searching Authority mailed Mar. 4, 2008.
PCT Application No. PCT/US2006/033724, International Search Report and Written Opinion of the International Searching Authority mailed Jan. 22, 2007.
PCT Application No. PCT/US2007/082382, International Preliminary Report on Patentability and Written Opinion of the International Searching Authority mailed May 7, 2009.
PCT Application No. PCT/US2007/082382, International Search Report and Written Opinion of the International Searching Authority mailed Jun. 24, 2008.
PCT Application No. PCT/US2007/082744, International Preliminary Report and Written Opinion of the International Searching Authority mailed May 7, 2009.
PCT Application No. PCT/US2007/082744, International Search Report and Written Opinion of the International Searching Authority mailed.
PCT Application No. PCT/US2009/058895, International Preliminary Report on Patentability mailed Apr. 14, 2011.
PCT Application No. PCT/US2009/058895, International Search Report and Written Opinion of the International Searching Authority mailed Nov. 20, 2009.
PCT Application No. PCT/US2010/022669, International Preliminary Report on Patentability and Written Opinion of the International Searching Authority mailed Aug. 11, 2011.
PCT Application No. PCT/US2010/022669, International Search Report and Written Opinion of the International Searching Authority mailed Mar. 23, 2010.
PCT Application No. PCT/US2010/031525, International Preliminary Report on Patentability and Written Opinion of the International Searching Authority mailed Oct. 27, 2011.
PCT Application No. PCT/US2010/031525, International Search Report and Written Opinion of the International Searching Authority mailed Jun. 10, 2010.
PCT Application No. PCT/US2010/054879, International Preliminary Report on Patentability and Written Opinion of the International Searching Authority mailed May 10, 2012.
PCT Application No. PCT/US2010/054879, International Search Report and Written Opinion of the International Searching Authority mailed Dec. 27, 2010.
PCT Application No. PCT/US2011/027794, International Preliminary Report on Patentability and Written Opinion of the International Searching Authority mailed Sep. 20, 2012.
PCT Application No. PCT/US2011/027794, International Search Report and Written Opinion of the International Searching Authority mailed May 4, 2011.
PCT Application No. PCT/US2012/062541, International Search Report and Written Opinion of the International Searching Authority mailed Dec. 31, 2012.
PCT Application No. PCT/US2012/072213, International Search Report and Written Opinion of the International Searching Authority mailed Mar. 19, 2013.
PCT Application No. PCT/US2013/055833, International Search Report and Written Opinion of the International Searching Authority mailed Jan. 29, 2014.
PCT Application No. PCT/US2013/057140, International Search Report and Written Opinion of the International Searching Authority mailed Dec. 6, 2013.
PCT Application No. PCT/US2013/060471, International Search Report and Written Opinion of the International Searching Authority mailed Feb. 10, 2014.
U.S. Appl. No. 11/552,935, Advisory Action mailed Jun. 26, 2009.
U.S. Appl. No. 11/552,935, Notice of Allowance Aug. 20, 2009.
U.S. Appl. No. 11/552,935, Office Action mailed Jun. 25, 2008.
U.S. Appl. No. 11/552,935, Office Action mailed Mar. 17, 2009.
U.S. Appl. No. 11/925,689, Advisory Action mailed Jun. 30, 2010.
U.S. Appl. No. 11/925,689, Notice of Allowance mailed Oct. 31, 2011.
U.S. Appl. No. 11/925,689, Office Action mailed Aug. 20, 2009.
U.S. Appl. No. 11/925,689, Office Action mailed Feb. 17, 2010.
U.S. Appl. No. 11/925,689, Office Action mailed Mar. 25, 2011.
U.S. Appl. No. 12/065,257, Office Action mailed Apr. 2, 2012.
U.S. Appl. No. 12/065,257, Office Action mailed Oct. 15, 2012.
U.S. Appl. No. 12/238,874, Notice of Allowance mailed May 15, 2012.

(56) References Cited

OTHER PUBLICATIONS

U.S. Appl. No. 12/238,874, Office Action mailed Aug. 18, 2011.
U.S. Appl. No. 12/238,874, Office Action mailed Feb. 6, 2012.
U.S. Appl. No. 12/242,823, Notice of Allowance mailed Apr. 27, 2012.
U.S. Appl. No. 12/242,823, Office Action mailed Apr. 6, 2012.
U.S. Appl. No. 13/418,305, Notice of Allowance mailed Jan. 17, 2014.

* cited by examiner

METHOD, SYSTEM AND COMPUTER PROGRAM PRODUCT FOR REAL-TIME DETECTION OF SENSITIVITY DECLINE IN ANALYTE SENSORS

CROSS-REFERENCE TO RELATED APPLICATIONS

The present application is a continuation of U.S. patent application Ser. No. 17/156,169, filed Jan. 22, 2021, which is a continuation of U.S. patent application Ser. No. 15/866,384, filed Jan. 9, 2018, now U.S. Pat. No. 10,903,914, which is a continuation of U.S. patent application Ser. No. 14/266,612, filed Apr. 30, 2014, now U.S. Pat. No. 9,882,660, which is a continuation of U.S. patent application Ser. No. 13/418,305, filed Mar. 12, 2012, now U.S. Pat. No. 8,718,958, which is a continuation of U.S. patent application Ser. No. 11/925,689, filed Oct. 26, 2007, now U.S. Pat. No. 8,135,548, which claims priority to U.S. Provisional Application No. 60/854,566, filed Oct. 26, 2006, all of which are incorporated herein by reference in their entireties for all purposes.

BACKGROUND

Analyte, e.g., glucose monitoring systems including continuous and discrete monitoring systems generally include a small, lightweight battery powered and microprocessor controlled system which is configured to detect signals proportional to the corresponding measured glucose levels using an electrometer, and RF signals to transmit the collected data. One aspect of certain analyte monitoring systems include a transcutaneous or subcutaneous analyte sensor configuration which is, for example, partially mounted on the skin of a subject whose analyte level is to be monitored. The sensor cell may use a two or three-electrode (work, reference and counter electrodes) configuration driven by a controlled potential (potentiostat) analog circuit connected through a contact system.

The analyte sensor may be configured so that a portion thereof is placed under the skin of the patient so as to detect the analyte levels of the patient, and another portion of segment of the analyte sensor that is in communication with the transmitter unit. The transmitter unit is configured to transmit the analyte levels detected by the sensor over a wireless communication link such as an RF (radio frequency) communication link to a receiver/monitor unit. The receiver/monitor unit performs data analysis, among others on the received analyte levels to generate information pertaining to the monitored analyte levels.

In view of the foregoing, it would be desirable to have an accurate assessment of the glucose level fluctuations, and in particular, the detection of analyte sensor signal dropouts of sensor sensitivity referred to as Early Signal Attenuation (ESA).

SUMMARY OF THE DISCLOSURE

In one embodiment, method, system and computer program product for receiving a plurality of analyte sensor related signals, determining a probability of signal attenuation associated with the received plurality of analyte sensor related signals, verifying the presence of signal attenuation when the determined probability exceeds a predetermined threshold level, and generating a first output signal associated with the verification of the presence of signal attenuation, are disclosed.

These and other objects, features and advantages of the present disclosure will become more fully apparent from the following detailed description of the embodiments, the appended claims and the accompanying drawings.

DETAILED DESCRIPTION

As described in further detail below, in accordance with the various embodiments of the present disclosure, there is provided method, system and computer program product for real time detection of analyte sensor sensitivity decline in data processing and control systems including, for example, analyte monitoring systems. In particular, within the scope of the present disclosure, there are provided method, system and computer program product for the detection of episodes of low sensor sensitivity that may cause clinically significant sensor related errors, including, for example, early sensor attenuation (ESA) represented by sensor sensitivity (defined as the ratio between the analyte sensor current level and the blood glucose level) decline which may exist during the initial 12-24 hours of the sensor life, or during night time use of the analyte sensor ("night time dropouts").

Figure 1:
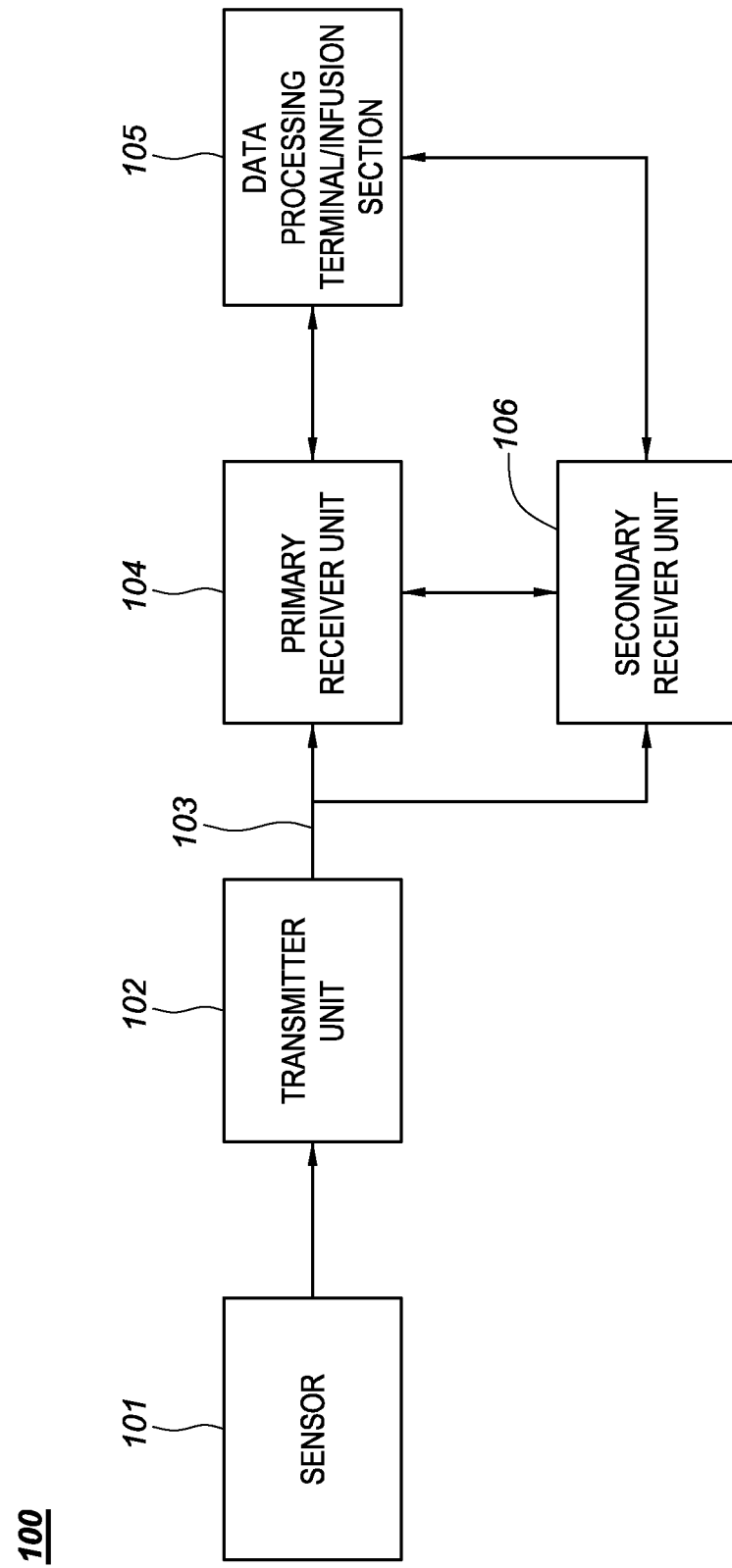
FIG. 1 illustrates a block diagram of a data monitoring and management system for practicing one or more embodiments of the present disclosure.

FIG. 1 illustrates a data monitoring and management system such as, for example, analyte (e.g., glucose) monitoring system 100 in accordance with one embodiment of the present disclosure. The subject disclosure is further described primarily with respect to a glucose monitoring system for convenience and such description is in no way intended to limit the scope of the disclosure. It is to be understood that the analyte monitoring system may be configured to monitor a variety of analytes, e.g., lactate, and the like.

Analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored.

The analyte monitoring system 100 includes a sensor 101, a transmitter unit 102 coupled to the sensor 101, and a primary receiver unit 104 which is configured to communicate with the transmitter unit 102 via a communication link 103. The primary receiver unit 104 may be further configured to transmit data to a data processing terminal 105 for evaluating the data received by the primary receiver unit 104. Moreover, the data processing terminal 105 in one embodiment may be configured to receive data directly from the transmitter unit 102 via a communication link which may optionally be configured for bi-directional communication.

Also shown in FIG. 1 is a secondary receiver unit 106 which is operatively coupled to the communication link 103 and configured to receive data transmitted from the transmitter unit 102. Moreover, as shown in FIG. 1, the secondary receiver unit 106 is configured to communicate with the primary receiver unit 104 as well as the data processing terminal 105. Indeed, the secondary receiver unit 106 may be configured for bi-directional wireless communication with each of the primary receiver unit 104 and the data processing terminal 105. As discussed in further detail below, in one embodiment of the present disclosure, the secondary receiver unit 106 may be configured to include a limited number of functions and features as compared with the primary receiver unit 104. As such, the secondary receiver unit 106 may be configured substantially in a smaller compact housing or embodied in a device such as a wrist watch, for example. Alternatively, the secondary receiver unit 106 may be configured with the same or substantially similar functionality as the primary receiver unit 104, and may be configured to be used in conjunction with a docking cradle unit for placement by bedside, for night time monitoring, and/or bi-directional communication device.

Only one sensor 101, transmitter unit 102, communication link 103, and data processing terminal 105 are shown in the embodiment of the analyte monitoring system 100 illustrated in FIG. 1. However, it will be appreciated by one of ordinary skill in the art that the analyte monitoring system 100 may include one or more sensor 101, transmitter unit 102, communication link 103, and data processing terminal 105. Moreover, within the scope of the present disclosure, the analyte monitoring system 100 may be a continuous monitoring system, or semi-continuous, or a discrete monitoring system. In a multi-component environment, each device is configured to be uniquely identified by each of the other devices in the system so that communication conflict is readily resolved between the various components within the analyte monitoring system 100.

In one embodiment of the present disclosure, the sensor 101 is physically positioned in or on the body of a user whose analyte level is being monitored. The sensor 101 may be configured to continuously sample the analyte level of the user and convert the sampled analyte level into a corresponding data signal for transmission by the transmitter unit 102. In one embodiment, the transmitter unit 102 is coupled to the sensor 101 so that both devices are positioned on the user's body, with at least a portion of the analyte sensor 101 positioned transcutaneously under the skin layer of the user. The transmitter unit 102 performs data processing such as filtering and encoding on data signals, each of which corresponds to a sampled analyte level of the user, for transmission to the primary receiver unit 104 via the communication link 103.

In one embodiment, the analyte monitoring system 100 is configured as a one-way RF communication path from the transmitter unit 102 to the primary receiver unit 104. In such embodiment, the transmitter unit 102 transmits the sampled data signals received from the sensor 101 without acknowledgement from the primary receiver unit 104 that the transmitted sampled data signals have been received. For example, the transmitter unit 102 may be configured to transmit the encoded sampled data signals at a fixed rate (e.g., at one minute intervals) after the completion of the initial power on procedure. Likewise, the primary receiver unit 104 may be configured to detect such transmitted encoded sampled data signals at predetermined time intervals. Alternatively, the analyte monitoring system 100 may be configured with a bi-directional RF (or otherwise) communication between the transmitter unit 102 and the primary receiver unit 104.

Additionally, in one aspect, the primary receiver unit 104 may include two sections. The first section is an analog interface section that is configured to communicate with the transmitter unit 102 via the communication link 103. In one embodiment, the analog interface section may include an RF receiver and an antenna for receiving and amplifying the data signals from the transmitter unit 102, which are thereafter, demodulated with a local oscillator and filtered through a band-pass filter. The second section of the primary receiver unit 104 is a data processing section which is configured to process the data signals received from the transmitter unit 102 such as by performing data decoding, error detection and correction, data clock generation, and data bit recovery.

In operation, upon completing the power-on procedure, the primary receiver unit 104 is configured to detect the presence of the transmitter unit 102 within its range based on, for example, the strength of the detected data signals received from the transmitter unit 102 or predetermined transmitter identification information. Upon successful synchronization with the corresponding transmitter unit 102, the primary receiver unit 104 is configured to begin receiving from the transmitter unit 102 data signals corresponding to the user's detected analyte level. More specifically, the primary receiver unit 104 in one embodiment is configured to perform synchronized time hopping with the corresponding synchronized transmitter unit 102 via the communication link 103 to obtain the user's detected analyte level.

Referring again to FIG. 1, the data processing terminal 105 may include a personal computer, a portable computer such as a laptop or a handheld device (e.g., personal digital assistants (PDAs)), and the like, each of which may be configured for data communication with the receiver via a wired or a wireless connection. Additionally, the data processing terminal 105 may further be connected to a data network (not shown) for storing, retrieving and updating data corresponding to the detected analyte level of the user.

Within the scope of the present disclosure, the data processing terminal 105 may include an infusion device such as an insulin infusion pump or the like, which may be configured to administer insulin to patients, and which may be configured to communicate with the receiver unit 104 for receiving, among others, the measured analyte level. Alternatively, the receiver unit 104 may be configured to integrate an infusion device therein so that the receiver unit 104 is configured to administer insulin therapy to patients, for example, for administering and modifying basal profiles, as well as for determining appropriate boluses for administration based on, among others, the detected analyte levels received from the transmitter unit 102.

Additionally, the transmitter unit 102, the primary receiver unit 104 and the data processing terminal 105 may each be configured for bi-directional wireless communication such that each of the transmitter unit 102, the primary receiver unit 104 and the data processing terminal 105 may be configured to communicate (that is, transmit data to and receive data from) with each other via a wireless communication link. More specifically, the data processing terminal 105 may in one embodiment be configured to receive data directly from the transmitter unit 102 via a communication link, where the communication link, as described above, may be configured for bi-directional communication.

In this embodiment, the data processing terminal 105 which may include an insulin pump, may be configured to receive the analyte signals from the transmitter unit 102, and thus, incorporate the functions of the receiver unit 104 including data processing for managing the patient's insulin therapy and analyte monitoring. In one embodiment, the communication link 103 may include one or more of an RF communication protocol, an infrared communication protocol, a Bluetooth® enabled communication protocol, an 802.11x wireless communication protocol, or an equivalent wireless communication protocol which would allow secure, wireless communication of several units (for example, per HIPAA requirements) while avoiding potential data collision and interference.

Figure 2:
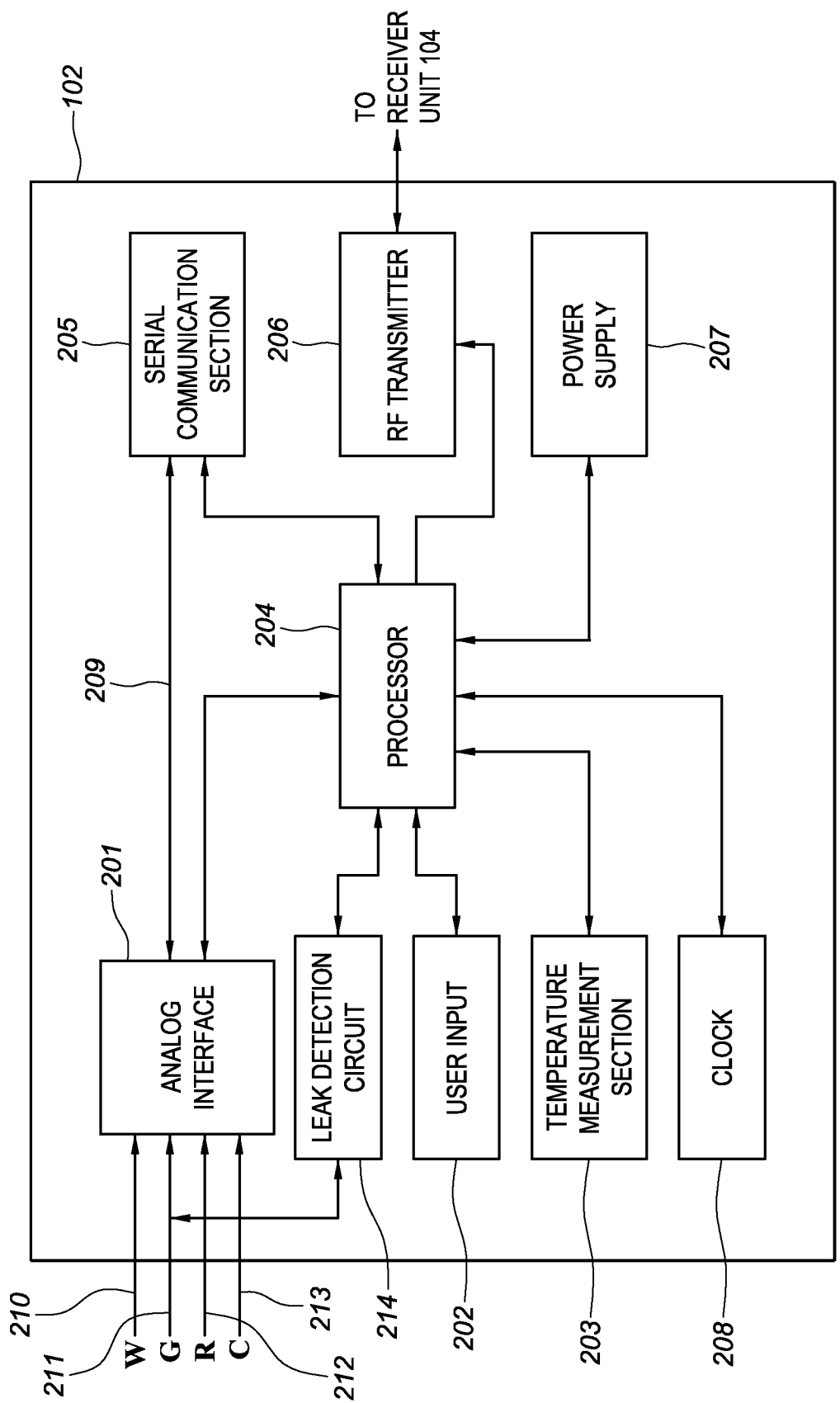
FIG. 2 is a block diagram of the transmitter unit of the data monitoring and management system shown in FIG. 1 in accordance with one embodiment of the present disclosure.

FIG. 2 is a block diagram of the transmitter of the data monitoring and detection system shown in FIG. 1 in accordance with one embodiment of the present disclosure. Referring to FIG. 2, the transmitter unit 102 in one embodiment includes an analog interface 201 configured to communicate with the sensor 101 (FIG. 1), a user input 202, and a temperature measurement section 203, each of which is operatively coupled to a transmitter processor 204 such as a central processing unit (CPU).

Further shown in FIG. 2 are a transmitter serial communication section 205 and an RF transmitter 206, each of which is also operatively coupled to the transmitter processor 204. Moreover, a power supply 207 such as a battery is also provided in the transmitter unit 102 to provide the necessary power for the transmitter unit 102. Additionally, as can be seen from FIG. 2, a clock 208 is provided to, among others, supply real time information to the transmitter processor 204.

As can be seen from FIG. 2, the sensor 101 (FIG. 1) is provided four contacts, three of which are electrodes—work electrode (W) 210, guard contact (G) 211, reference electrode (R) 212, and counter electrode (C) 213, each operatively coupled to the analog interface 201 of the transmitter unit 102. In one embodiment, each of the work electrode (W) 210, guard contact (G) 211, reference electrode (R) 212, and counter electrode (C) 213 may be made using a conductive material that is either printed or etched, for example, such as carbon which may be printed, or metal foil (e.g., gold) which may be etched, or alternatively provided on a substrate material using laser or photolithography.

In one embodiment, a unidirectional input path is established from the sensor 101 (FIG. 1) and/or manufacturing and testing equipment to the analog interface 201 of the transmitter unit 102, while a unidirectional output is established from the output of the RF transmitter 206 of the transmitter unit 102 for transmission to the primary receiver unit 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, via the data path described above, the transmitter unit 102 is configured to transmit to the primary receiver unit 104 (FIG. 1), via the communication link 103 (FIG. 1), processed and encoded data signals received from the sensor 101 (FIG. 1). Additionally, the unidirectional communication data path between the analog interface 201 and the RF transmitter 206 discussed above allows for the configuration of the transmitter unit 102 for operation upon completion of the manufacturing process as well as for direct communication for diagnostic and testing purposes.

As discussed above, the transmitter processor 204 is configured to transmit control signals to the various sections of the transmitter unit 102 during the operation of the transmitter unit 102. In one embodiment, the transmitter processor 204 also includes a memory (not shown) for storing data such as the identification information for the transmitter unit 102, as well as the data signals received from the sensor 101. The stored information may be retrieved and processed for transmission to the primary receiver unit 104 under the control of the transmitter processor 204. Furthermore, the power supply 207 may include a commercially available battery.

The transmitter unit 102 is also configured such that the power supply section 207 is capable of providing power to the transmitter for a minimum of about three months of continuous operation after having been stored for about eighteen months in a low-power (non-operating) mode. In one embodiment, this may be achieved by the transmitter processor 204 operating in low power modes in the non-operating state, for example, drawing no more than approximately 1 μA of current. Indeed, in one embodiment, the final step during the manufacturing process of the transmitter unit 102 may place the transmitter unit 102 in the lower power, non-operating state (i.e., post-manufacture sleep mode). In this manner, the shelf life of the transmitter unit 102 may be significantly improved. Moreover, as shown in FIG. 2, while the power supply unit 207 is shown as coupled to the processor 204, and as such, the processor 204 is configured to provide control of the power supply unit 207, it should be noted that within the scope of the present disclosure, the power supply unit 207 is configured to provide the necessary power to each of the components of the transmitter unit 102 shown in FIG. 2.

Referring back to FIG. 2, the power supply section 207 of the transmitter unit 102 in one embodiment may include a rechargeable battery unit that may be recharged by a separate power supply recharging unit (for example, provided in the receiver unit 104) so that the transmitter unit 102 may be powered for a longer period of usage time. Moreover, in one embodiment, the transmitter unit 102 may be configured without a battery in the power supply section 207, in which case the transmitter unit 102 may be configured to receive power from an external power supply source (for example, a battery) as discussed in further detail below.

Referring yet again to FIG. 2, the temperature measurement section 203 of the transmitter unit 102 is configured to monitor the temperature of the skin near the sensor insertion site. The temperature reading is used to adjust the analyte readings obtained from the analog interface 201. The RF transmitter 206 of the transmitter unit 102 may be configured for operation in the frequency band of 315 MHz to 322 MHz, for example, in the United States. Further, in one embodiment, the RF transmitter 206 is configured to modulate the carrier frequency by performing Frequency Shift Keying and Manchester encoding. In one embodiment, the data transmission rate is 19,200 symbols per second, with a minimum transmission range for communication with the primary receiver unit 104.

Referring yet again to FIG. 2, also shown is a leak detection circuit 214 coupled to the guard contact (G) 211 and the processor 204 in the transmitter unit 102 of the data monitoring and management system 100. The leak detection circuit 214 in accordance with one embodiment of the present disclosure may be configured to detect leakage current in the sensor 101 to determine whether the measured sensor data is corrupt or whether the measured data from the sensor 101 is accurate.

Figure 3:
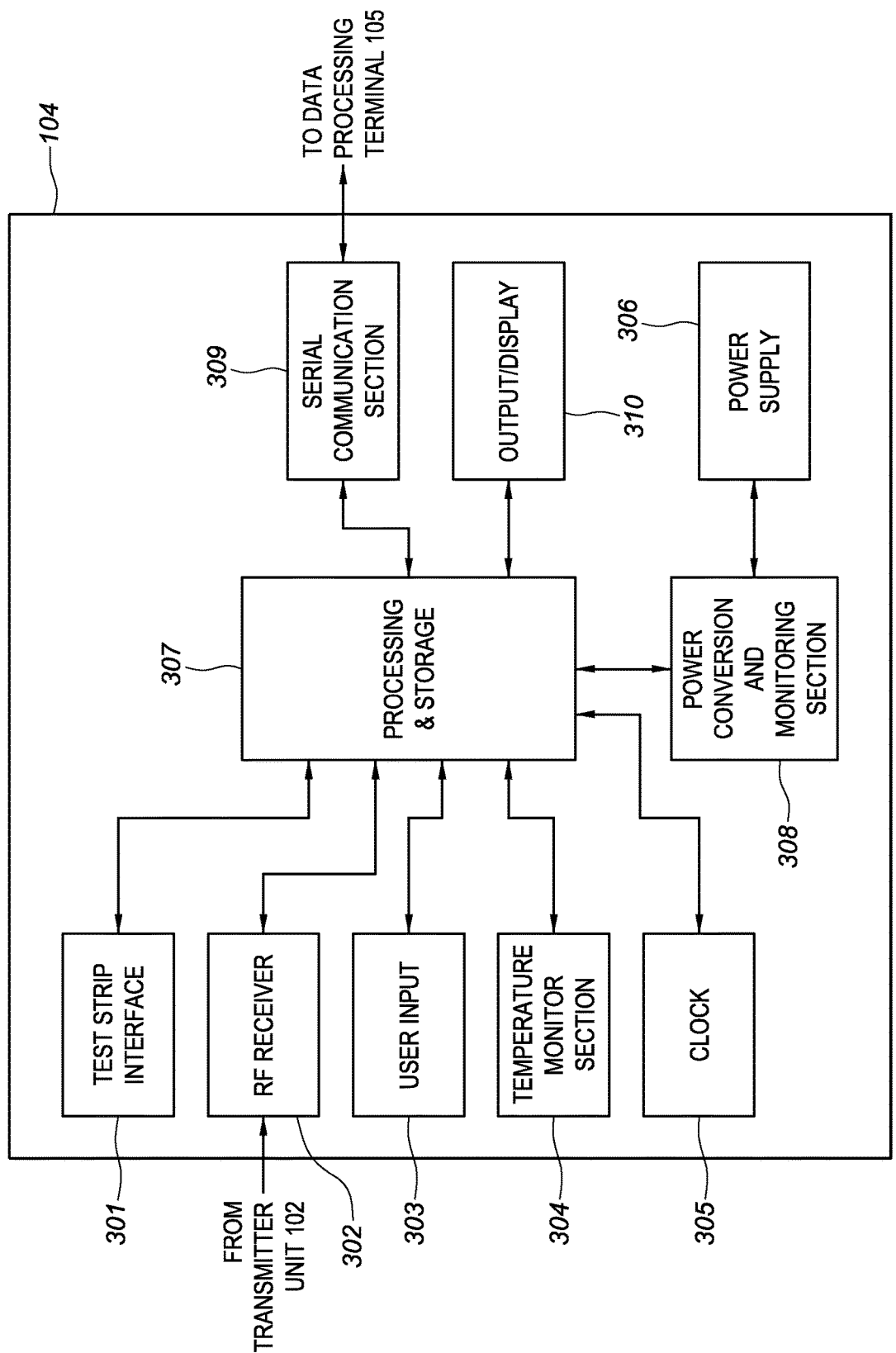
FIG. 3 is a block diagram of the receiver/monitor unit of the data monitoring and management system shown in FIG. 1 in accordance with one embodiment of the present disclosure.

FIG. 3 is a block diagram of the receiver/monitor unit of the data monitoring and management system shown in FIG. 1 in accordance with one embodiment of the present disclosure. Referring to FIG. 3, the primary receiver unit 104 includes a blood glucose test strip interface 301, an RF receiver 302, an input 303, a temperature monitor section 304, and a clock 305, each of which is operatively coupled to a receiver processor 307. As can be further seen from FIG. 3, the primary receiver unit 104 also includes a power supply 306 operatively coupled to a power conversion and monitoring section 308. Further, the power conversion and monitoring section 308 is also coupled to the receiver processor 307. Moreover, also shown are a receiver serial communication section 309, and an output 310, each operatively coupled to the receiver processor 307.

In one embodiment, the test strip interface 301 includes a glucose level testing portion to receive a manual insertion of a glucose test strip, and thereby determine and display the glucose level of the test strip on the output 310 of the primary receiver unit 104. This manual testing of glucose can be used to calibrate sensor 101. The RF receiver 302 is configured to communicate, via the communication link 103 (FIG. 1) with the RF transmitter 206 of the transmitter unit 102, to receive encoded data signals from the transmitter unit 102 for, among others, signal mixing, demodulation, and other data processing. The input 303 of the primary receiver unit 104 is configured to allow the user to enter information into the primary receiver unit 104 as needed. In one aspect, the input 303 may include one or more keys of a keypad, a touch-sensitive screen, or a voice-activated input command unit. The temperature monitor section 304 is configured to provide temperature information of the primary receiver unit 104 to the receiver processor 307, while the clock 305 provides, among others, real time information to the receiver processor 307.

Each of the various components of the primary receiver unit 104 shown in FIG. 3 is powered by the power supply 306 which, in one embodiment, includes a battery. Furthermore, the power conversion and monitoring section 308 is configured to monitor the power usage by the various components in the primary receiver unit 104 for effective power management and to alert the user, for example, in the event of power usage which renders the primary receiver unit 104 in sub-optimal operating conditions. An example of such sub-optimal operating condition may include, for example, operating the vibration output mode (as discussed below) for a period of time thus substantially draining the power supply 306 while the processor 307 (thus, the primary receiver unit 104) is turned on. Moreover, the power conversion and monitoring section 308 may additionally be configured to include a reverse polarity protection circuit such as a field effect transistor (FET) configured as a battery activated switch.

The serial communication section 309 in the primary receiver unit 104 is configured to provide a bi-directional communication path from the testing and/or manufacturing equipment for, among others, initialization, testing, and configuration of the primary receiver unit 104. Serial communication section 309 can also be used to upload data to a computer, such as time-stamped blood glucose data. The communication link with an external device (not shown) can be made, for example, by cable, infrared (IR) or RF link. The output 310 of the primary receiver unit 104 is configured to provide, among others, a graphical user interface (GUI) such as a liquid crystal display (LCD) for displaying information. Additionally, the output 310 may also include an integrated speaker for outputting audible signals as well as to provide vibration output as commonly found in handheld electronic devices, such as mobile telephones presently available. In a further embodiment, the primary receiver unit 104 also includes an electro-luminescent lamp configured to provide backlighting to the output 310 for output visual display in dark ambient surroundings.

Referring back to FIG. 3, the primary receiver unit 104 in one embodiment may also include a storage section such as a programmable, non-volatile memory device as part of the processor 307, or provided separately in the primary receiver unit 104, operatively coupled to the processor 307. The processor 307 is further configured to perform Manchester decoding as well as error detection and correction upon the encoded data signals received from the transmitter unit 102 via the communication link 103.

In a further embodiment, the one or more of the transmitter unit 102, the primary receiver unit 104, secondary receiver unit 106, or the data processing terminal/infusion section 105 may be configured to receive the blood glucose value wirelessly over a communication link from, for example, a glucose meter. In still a further embodiment, the user or patient manipulating or using the analyte monitoring system 100 (FIG. 1) may manually input the blood glucose value using, for example, a user interface (for example, a keyboard, keypad, and the like) incorporated in the one or more of the transmitter unit 102, the primary receiver unit 104, secondary receiver unit 106, or the data processing terminal/infusion section 105.

Additional detailed description of the continuous analyte monitoring system, its various components including the functional descriptions of the transmitter are provided in U.S. Pat. No. 6,175,752 issued Jan. 16, 2001 entitled "Analyte Monitoring Device and Methods of Use", and in application Ser. No. 10/745,878 filed Dec. 26, 2003 entitled "Continuous Glucose Monitoring System and Methods of Use", each assigned to Abbott Diabetes Care Inc., of Alameda, California.

Figure 4A:
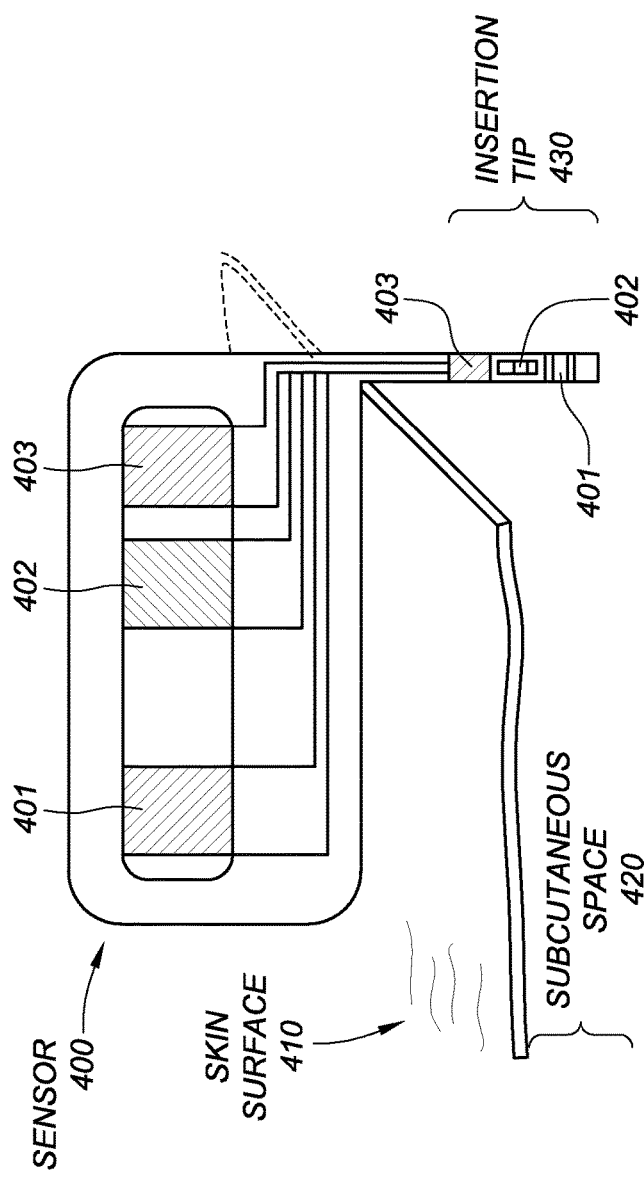
FIGS. 4A-4B illustrate a perspective view and a cross sectional view, respectively of an analyte sensor in accordance with one embodiment of the present disclosure.
Figure 4B:
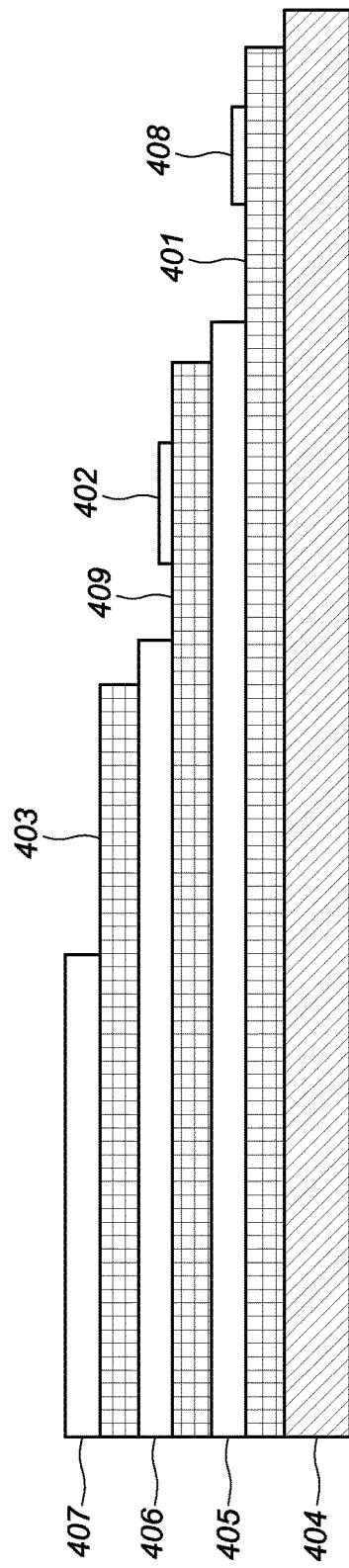

FIGS. 4A-4B illustrate a perspective view and a cross sectional view, respectively of an analyte sensor in accordance with one embodiment of the present disclosure. Referring to FIG. 4A, a perspective view of a sensor 400, the major portion of which is above the surface of the skin 410, with an insertion tip 430 penetrating through the skin and into the subcutaneous space 420 in contact with the user's biofluid such as interstitial fluid. Contact portions of a working electrode 401, a reference electrode 402, and a counter electrode 403 can be seen on the portion of the sensor 400 situated above the skin surface 410. Working electrode 401, a reference electrode 402, and a counter electrode 403 can be seen at the end of the insertion tip 430.

Referring now to FIG. 4B, a cross sectional view of the sensor 400 in one embodiment is shown. In particular, it can be seen that the various electrodes of the sensor 400 as well as the substrate and the dielectric layers are provided in a stacked or layered configuration or construction. For example, as shown in FIG. 4B, in one aspect, the sensor 400 (such as the sensor 101 FIG. 1), includes a substrate layer 404, and a first conducting layer 401 such as a carbon trace disposed on at least a portion of the substrate layer 404, and which may comprise the working electrode. Also shown disposed on at least a portion of the first conducting layer 401 is a sensing layer 408.

Referring back to FIG. 4B, a first insulation layer such as a first dielectric layer 405 is disposed or stacked on at least a portion of the first conducting layer 401, and further, a second conducting layer 409 such as another carbon trace may be disposed or stacked on top of at least a portion of the first insulation layer (or dielectric layer) 405. As shown in FIG. 4B, the second conducting layer 409 may comprise the reference electrode 402, and in one aspect, may include a layer of silver/silver chloride (Ag/AgCl).

Referring still again to FIG. 4B, a second insulation layer 406 such as a dielectric layer in one embodiment may be disposed or stacked on at least a portion of the second conducting layer 409. Further, a third conducting layer 403 which may include carbon trace and that may comprise the counter electrode may in one embodiment be disposed on at least a portion of the second insulation layer 406. Finally, a third insulation layer 407 is disposed or stacked on at least a portion of the third conducting layer 403. In this manner, the sensor 400 may be configured in a stacked or layered construction or configuration such that at least a portion of each of the conducting layers is separated by a respective insulation layer (for example, a dielectric layer).

Additionally, within the scope of the present disclosure, some or all of the electrodes 401, 402, 403 may be provided on the same side of the substrate 404 in a stacked construction as described above, or alternatively, may be provided in a co-planar manner such that each electrode is disposed on the same plane on the substrate 404, however, with a dielectric material or insulation material disposed between the conducting layers/electrodes. Furthermore, in still another aspect of the present disclosure, the one or more conducting layers such as the electrodes 401, 402, 403 may be disposed on opposing sides of the substrate 404.

Figure 5:
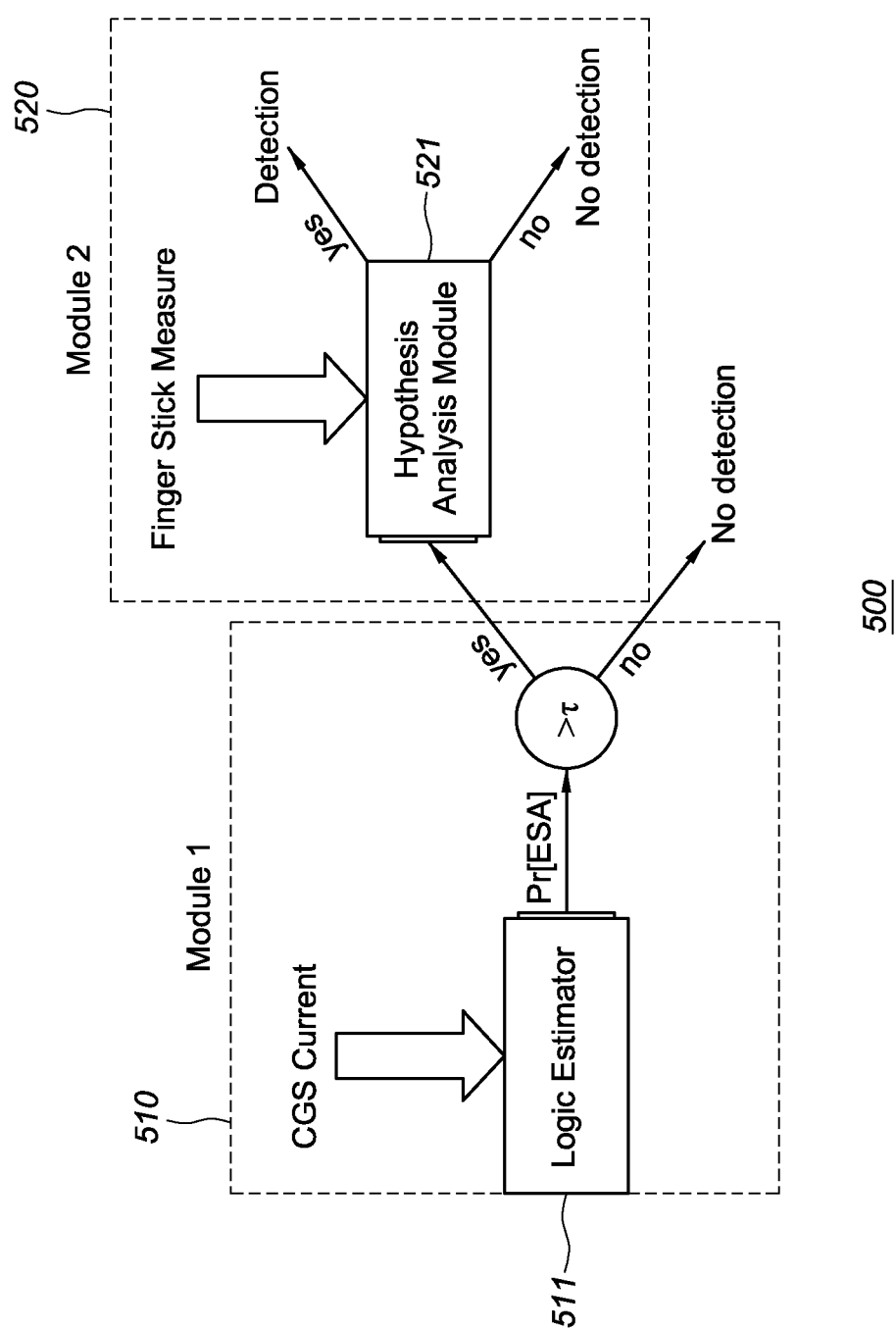
FIG. 5 is a block diagram illustrating real time early signal attenuation (ESA) in one embodiment of the present disclosure.

FIG. 5 is a block diagram illustrating real time early signal attenuation (ESA) in one embodiment of the present disclosure. Referring to FIG. 5, in one embodiment, the overall sensitivity decline detector 500 includes a first module 510 configured to perform an estimation of the probability of sensitivity decline based on a window of analyte sensor measurements to determine whether a finger stick measurement of blood glucose level is necessary. Based on the estimated probability of the sensitivity decline performed by the first module 510, when it is determined that the finger stick measurement of the blood glucose level is necessary, as shown in FIG. 5, in one aspect of the present disclosure, the second module 520 uses the measured blood glucose value to verify or otherwise confirm or reject the estimated probability of the sensitivity decline performed by the first module 510. In one aspect, the second module 520 may be configured to confirm or reject the results of the first module 510 (e.g., the estimated probability of sensitivity decline) based upon a statistical determination.

That is, in one aspect, the first module 510 of the sensitivity decline detector 500 of FIG. may be configured to estimate the probability of the analyte sensor sensitivity decline based on an analysis of a window of sensor values (for example, current signals from the analyte sensor for a predetermined time period). More specifically, the first module 510 may be configured to estimate the probability of the sensor sensitivity decline based on a sliding window extractor of sensor current signal characteristics, a model based estimation of the probability of sensitivity decline based on the determined or retrieved sensor current signal characteristics, and/or a comparison of the estimated probability to a predetermined threshold value T.

Referring back to FIG. 5, the logistic estimator 511 of the first module 510 may be configured in one embodiment to retrieve or extract a sliding window of sensor current signal characteristics, and to perform the estimation of the probability of the sensitivity decline based on the sensor current signal characteristics, and to compare the estimated probability of the sensitivity decline to a predetermined threshold T to determine, whether verification of the estimated sensitivity decline is desired, or whether it can be confirmed that ESA or night time drop outs is not detected based on the estimated probability of the sensitivity decline.

Referring again to FIG. 5, as shown, when it is determined that confirmation or verification of the estimated probability of the sensitivity decline is desired (based on, for example, when the estimated probability exceeds the predetermined threshold value T determined in the first module 510), hypothesis analysis module 521 of the second module 520 in the sensitivity decline detector 500 in one embodiment receives the capillary blood measurement from a blood glucose measurement device such as a blood glucose meter including FreesStyle® Lite, Freestyle Flash®, FreeStyle Freedom®, or Precision Xtra blood glucose meters commercially available from Abbott Diabetes Care Inc., of Alameda, California. In one aspect, based on the received capillary blood glucose measurement and the analyte sensor current characteristics or values, the estimated probability of the sensor sensitivity decline may be confirmed or rejected, thus confirming the presence of ESA or night time drop out (in the event the corresponding data point is associated with night time sensor current value), or alternatively, confirming that the ESA or night time drop out is not present.

In the manner described, in one aspect of the present disclosure, there is provided a real time detection routine based on sensor current signal characteristics, where the detector 500 (FIG. 5) includes a first module 510 configured in one embodiment to perform the detection and estimation of the probability of the sensor sensitivity decline, and a second module 520 configured in one aspect to verify the presence or absence of ESA or night time dropouts based on the probability estimations determined by the first module 510. Accordingly, in one aspect of the present disclosure, ESA episodes or night time declines or dropouts may be accurately detected while minimizing the potential for false alarms or false negatives.

Referring again to FIG. 5, a sliding window process is used in the first module 510 of the sensor sensitivity estimator 500 in one embodiment to mitigate between the desire for a real time decision process and the necessity of redundancy for sensor current characteristics estimation. An example of the sliding window process is illustrated in accordance with one embodiment of the present disclosure in FIG. 9.

For instance, in one aspect, during the processing performed by the first module 510, at each iteration of the decision process, a time window is selected, and based on the sensor current signals determined during the selected time window, one or more predetermined sensor characteristics are determined. By way of nonlimiting examples, the one or more predetermined sensor characteristics may include the mean current signal level, the current signal variance, the average slope of the current signal, and the average sensor life (or the time elapsed since the insertion or transcutaneous positioning of the analyte sensor).

Thereafter, the selected time window is then slid by a fixed number of minutes for the next iteration. In one aspect, the width or duration of the time window and the incremental step size may be predetermined or established to 60 minutes, thus generating non-overlapping time windows to minimize potential correlation between decisions. Within the scope of the present disclosure, other approaches may be contemplated, for example, where the sliding time windows may include time duration of approximately 30 minutes with an incremental one minute step.

In one aspect, the following expressions may be used to determine the sensor characteristic estimations discussed above such as, for example, the sensor signal mean, the average slope and the variance values:

$$\begin{bmatrix} \text{mean} \\ \text{slope} \end{bmatrix} = (X' X)^{-1} X' Y$$

where X is a matrix with a column of 1s and a column of data index and Y is a column vector of current values $$\text{variance} = \frac{1}{n-1} \sum_{i=0}^{\text{width}} (\text{current}_{t+1} - \text{mean})^2$$

where t is the index of the first available data point in the time window.

Referring back to FIG. 5, after estimating or determining the sensor characteristics described above, a four-dimensional feature vector corresponding to a time window of sensor current signal is generated. In one aspect, the generated feature vector and logistic regression approach may be used to estimate the probability that the sensor is undergoing or experiencing early signal attenuation (ESA) during each of the predetermined time window. In one aspect, the logistic regression approach for determination or estimation of the probability of ESA presence Pr[ESA] may be expressed as follows:

$$Pr[ESA \mid x_n] = \frac{\exp^{\langle \beta, x_n \rangle}}{1 + \exp^{\langle \beta, x_n \rangle}} \tag{1}$$

$$x_n = \begin{bmatrix} 1 \\ \log(\text{mean}_n) \\ \log(\text{variance}_n) \\ \text{slope}_n \\ \log(\text{sensorlife}_n) \end{bmatrix}$$

Figure 10:
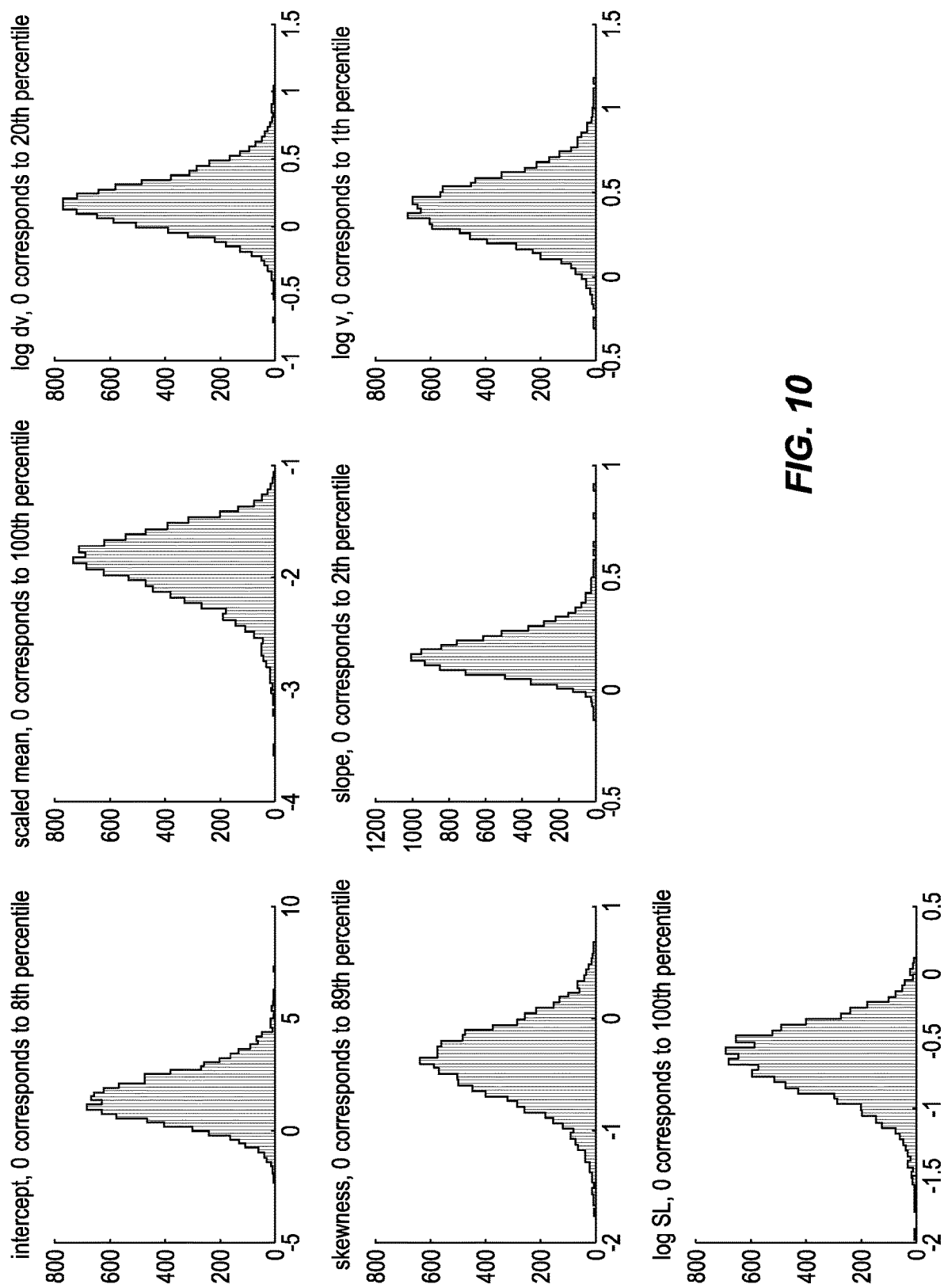
FIG. 10 illustrates bootstrap estimation of coefficients for module 1 of FIG. 5 in accordance with one embodiment of the present disclosure.

In one aspect, the coefficient vector β plays a significant role in the efficiency of the sensor signal attenuation estimation. That is, in one embodiment, a predetermined number of sensor insertions may be used to empirically determine or estimate the model coefficients. More specifically, in one aspect, a bootstrap estimation procedure may be performed to add robustness to the model coefficients. For example, a generalized linear model fit approach may be applied to a predetermined time period to determine the coefficient vector β. Based on a predefined number of iterations, an empirical probability distribution function of each coefficient may be determined, for example, as shown in FIG. 10, where each selected coefficient corresponds to the mode of the associated distribution.

After the determination of the one or more sensor current characteristics or parameters, and the determination of the corresponding coefficients, the probability of ESA presence Pr[ESA] is estimated based on, in one embodiment, the following expression:

$$Pr[ESA \mid x_n] = \frac{\exp^{1.511-1.813 \times \log(mean)+0.158 \times slope+0.399 \times \log(variance)-0.57 \times \log(SensorLife)}}{1 + \exp^{1.511-1.813 \times \log(mean)+0.158 \times slope+0.399 \times \log(variance)-0.57 \times \log(SensorLife)}} \tag{2}$$

It is to be noted that within the scope of the present disclosure, the estimation of the probability of the ESA presence Pr[ESA] as described by the function shown above may be modified depending upon the design or the associated underlying parameters, such as, for example, the time of day information, or the detrended variance of the sensor current signal, among others.

Referring yet again to FIG. 5, after the determination of the probability of ESA presence based on the estimation described above, in one aspect, the estimated probability is compared to a preselected threshold level, and based on the comparison, a request for capillary blood glucose measurement may be prompted. In one aspect, the predetermined threshold level may include 0.416 for comparison with the estimated probability of ESA presence. Alternatively, within the scope of the present disclosure, the predetermined threshold level may vary within the range of approximately 0.3 to 0.6.

As described above, in one aspect of the present disclosure, the first module 510 of the sensor sensitivity estimator 500 (FIG. 5) is configured to perform estimation of the probability of ESA presence based on the characteristics or parameters associated with the analyte sensor and the sensor current signals. In one embodiment, the second module 520 of the sensor sensitivity estimator 500 (FIG. 5) may be configured to perform additional processing based on capillary blood glucose measurement to provide substantially real time estimation of the early sensor attenuation (ESA) of the analyte sensors. That is, since ESA is defined by a drop or decrease of sensitivity (that is, the current signal of the sensor over the blood glucose ratio), the distribution of the sensitivity during ESA occurrence is generally lower than the distribution during normal functioning conditions. Additionally, based on the non linear relationship between the sensor current level and blood glucose measurements, the ESA presence probability estimation using capillary blood measurements may be determined using a bin (e.g., category) construction approach, as well as the estimation of the empirical distribution functions of the nominal sensitivity ratio.

More particularly, in one aspect of the present disclosure, the instantaneous sensitivity (IS) may be defined as the ratio of the actual current value of the analyte sensor and the actual blood glucose value at a given point in time (defined, for example, by the expression (a) below. However, due to noise in the signals, for example, particularly in the case of a stand alone measurement such as a single blood glucose measurement, the instantaneous sensitivity (IS) may be approximated by determining the average sensor current signal levels around the time of the fingerstick blood glucose determination, for example, by the expression (b) shown below.

a. $DS_t = \dfrac{\text{current}_t}{BG_t}$ (3)

b. $IS_t = \dfrac{\dfrac{1}{11}\sum_{i=-5}^{5}\text{current}_{t+i}}{BG_t}$

Given that each analyte sensor has a different sensitivity, and thus the instantaneous sensitivity (IS) is highly sensor dependent, the absolute value of the instantaneous sensitivity (IS) may not provide reliable indication of ESA presence. On the other hand, during manufacturing, each analyte sensor is associated with a nominal sensitivity value. Accordingly, the ratio of the instantaneous sensitivity over the sensor nominal sensitivity will result in a more sensor independent, reliable ESA detection mechanism. Accordingly, the sensitivity ratio Rs(t) at time t may be defined in one aspect as follows:

$R_{S(t)} = \dfrac{IS(t)}{S_{nominal}} = \dfrac{1}{11}\dfrac{\sum_{i=-5}^{5}\text{current}_{t+i}}{S_{nominal} \times BG_t}$ (4)

Figure 11:
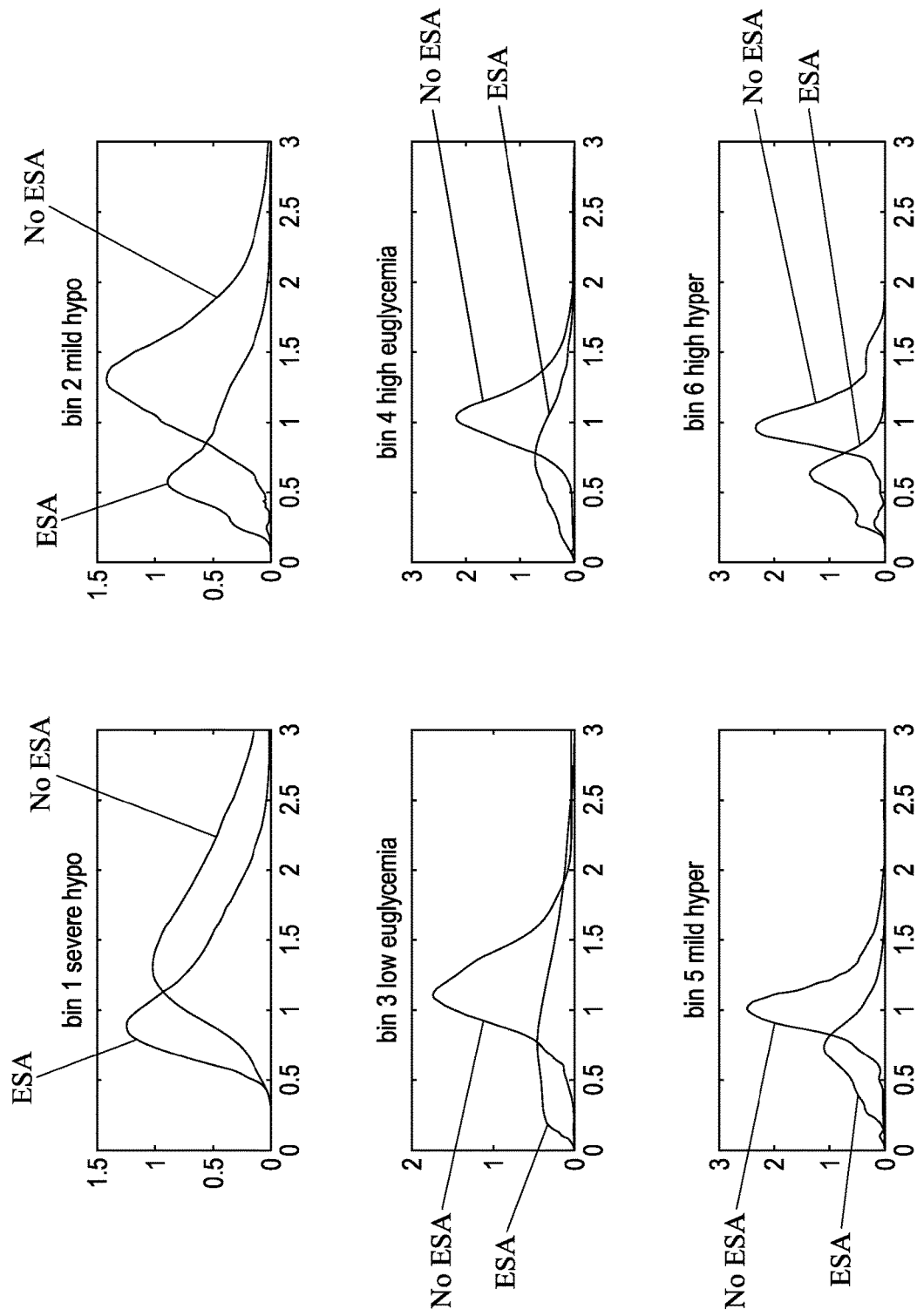
FIG. 11 illustrates Gaussian kernel estimation of the normalized sensitivity density of module 2 of FIG. 5 in accordance with one embodiment of the present disclosure.

Referring to the discussion above, the blood glucose bin/category construction approach in one embodiment may include defining a transformation of the blood glucose measurement scale which rectifies a discrepancy between the measured and estimated blood glucose values. That is, in one aspect, the defined transformation approach corresponds to or is associated with a typical distribution of blood glucose levels. For example, the transformation approach defining the various bins/categories may be determined based on the following expression:

$r = 1.509 \times e^{1.084 \times \log(\log(BG) - 5.381)}$ where $BG$ is in mg/dl (5)

where the following scaled glucose bins may be defined:

1. $r < -2$, severe hypoglycemia
2. $-2 \leq r < -1$, mild hypoglycemia
3. $-1 \leq r < 0$, low euglycemia
4. $0 \leq r < 1$, high euglycemia
5. $1 \leq r < 2$, mild hyperglycemia
6. $2 \leq r$, severe hyperglycemia Upon determination of the bin/category for use with the estimation of the probability of ESA presence, in one aspect, kernel density estimation (using Gaussian kernel, 24, for example) may be used to estimate the distribution of the sensitivity ratio Rs in each bin/category described above. In one aspect, this estimation of the distribution in sensitivity ratio Rs is shown in FIG. 11, where for each bin/category (including, for example, severe hypoglycemia (bin1), mild hypoglycemia (bin2), low euglycemia (bin3), high euglycemia (bin4), mild hyperglycemia (bin5), and high hyperglycemia (bin6)), each chart illustrates the associated distribution where ESA presence is detected.

Referring again to the discussions above, based on the estimation of the probability density functions of the estimated distribution of the sensitivity ratio Rs in each bin/category, in one aspect, a non-parametric hypothesis testing approach based on Bayes' law may be implemented. For example, in one aspect of the present disclosure, from Bayes' law, the estimated probability of ESA presence knowing the sensitivities ratio and the blood glucose bin/category may be decomposed based on the following expression:

$$Pr[ESA \mid R_s = \rho \text{ \& } r \in \text{bin}_i] = \dfrac{\pi_{ESA}\hat{f}_i(\rho)}{\pi_{ESA}\hat{f}_{ESA,i}(\rho) + \pi_{\overline{ESA}}\hat{f}_{\overline{ESA},i}(\rho)}$$ (6)

where $\pi_a$ is the proportion of events in class a and $\hat{f}_{a,i}$ is the previously estimated probability density function of Rs in bin/category i for class a.

In addition, to minimize the overall probability of error, the following decision rule may be applied:

sensor is ESA if $\dfrac{Pr[ESA \mid R_s = \rho \text{ \& } r \in \text{bin}_i]}{Pr[\overline{ESA} \mid R_s = \rho \text{ \& } r \in \text{bin}_i]} > 1 \Rightarrow$ (7)

$\dfrac{\hat{f}_{ESA,i}(\rho)}{\hat{f}_{\overline{ESA},i}(\rho)} > \dfrac{\pi_{\overline{ESA}}}{\pi_{ESA}}$ assuming $\pi_{\overline{ESA}} =$ $\pi_{ESA} = 0.5 \Rightarrow \dfrac{\hat{f}_{ESA,i}(\rho)}{\hat{f}_{\overline{ESA},i}(\rho)} > 1 \Rightarrow \hat{f}_{ESA,i}(\rho) > \hat{f}_{\overline{ESA},i}(\rho)$ Accordingly, based on the above, the hypothesis analysis module (521) of the second module 520 shown in FIG. 5 in one embodiment may be configured to verify/confirm the presence of ESA for a given analyte sensor based on the capillary blood glucose level measurement reading, when the capillary blood glucose measurement is in bin/category i, when the sensitivity ratio Rs is less than the corresponding defined threshold level $t_i$. For example, given the six blood glucose bins/categories (bin1 to bin6) described above, the respective threshold level $t_i$ is: $t_1=1.138$, $t_2=0.853$, $t_3=0.783$, $t_4=0.784$, $t_5=0.829$, and $t_6=0.797$.

In this manner, in one aspect of the present disclosure, the method, system and computer program product provides for, but not limited to, early detection of sensitivity drops in continuous glucose monitoring systems. Sensitivity drops can be found in the first 24 hours, for example, of the sensor life, and while the potential adverse impacts may be minimized by frequent calibration or sensor masking, such sensitivity drops have clinically significant effects on the accuracy of the sensor data, and in turn, potential danger to the patient using the sensor. Accordingly, in one aspect, there is provided method, system, and computer program product for estimating or determining the probability of the presence of ESA based on the sensor current signal characteristics, and thereafter, performing a confirmation or verification routine to determine whether the sensitivity drop probability estimated based on the sensor current signal characteristics corresponds to a real time occurrence of a corresponding sensitivity drop in the sensor.

Accordingly, sensor accuracy, and in particular in the critical hypoglycemic ranges may be improved, multiple calibrations and/or sensor masking may be avoided during the early stages of the sensor life, and further, sensor calibration during sensitivity drop occurrence which may result in undetected hypoglycemic events, may be avoided.

Figure 6:
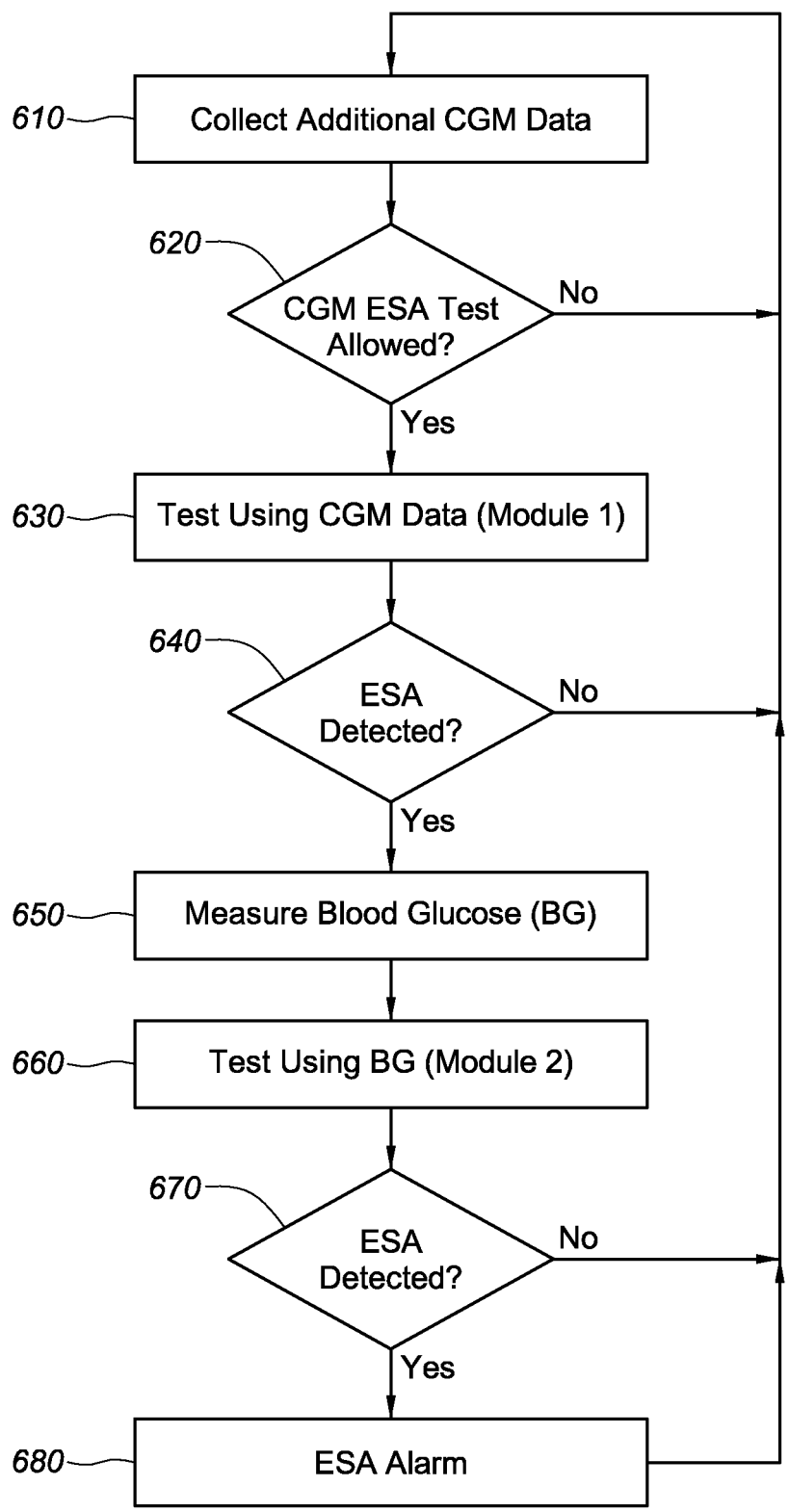
FIG. 6 is a flowchart illustrating an overall ESA detection routine in accordance with one embodiment of the present disclosure.

FIG. 6 is a flowchart illustrating an overall ESA detection routine in accordance with one embodiment of the present disclosure. Referring to FIG. 6, in one embodiment of the present disclosure, a predetermined number of sensor data is retrieved or collected (610), and thereafter, it is determined whether the probability estimation for the sensitivity decline determination is appropriate (620). In one aspect, one or more of the following parameters may be used to determine whether the determination of the probability estimation of the sensitivity decline is appropriate: presence or collection of sufficient data points associated with the analyte sensor, timing of the probability estimation relative to when the analyte sensor was inserted or subcutaneously positioned, time period since the most recent determination of the probability estimation for the sensitivity decline, among others.

If it is determined that the probability estimation for the sensitivity decline determination is not appropriate (620), then the routine shown in FIG. 6 returns to collecting additional sensor data points. On the other hand, if it is determined that the probability estimation for the sensitivity decline determination is appropriate, then the probability estimation for the sensitivity decline determination is performed (630). Thereafter, based upon the determined probability estimation for the sensitivity decline, it is determined whether ESA is present or not (640).

That is, based on the analysis performed, for example, by the first module 510 of the sensitivity decline detector 500 (FIG. 5), if ESA is not detected, then the routine returns to collection and/or retrieval of additional sensor current data (610). On the other hand, if based on the analysis described above ESA is detected (640), then a capillary blood measurement is requested (for example, by prompting the user to perform a fingerstick blood glucose test and input the blood glucose value) (650). Thereafter, the routine shown in FIG. 6 performs the routine for confirming the presence or absence of ESA (660) by, for example, the hypothesis analysis module 521 (FIG. 5).

Referring again to FIG. 6, if based on the analysis using the capillary blood measurement determines that ESA is not present (670), the routine again returns to the data collection/retrieval mode (610). On the other hand, if ESA presence is determined (670), in one aspect, an alarm or notification may be generated and provided to the user (680) to alert the user.

Figure 7:
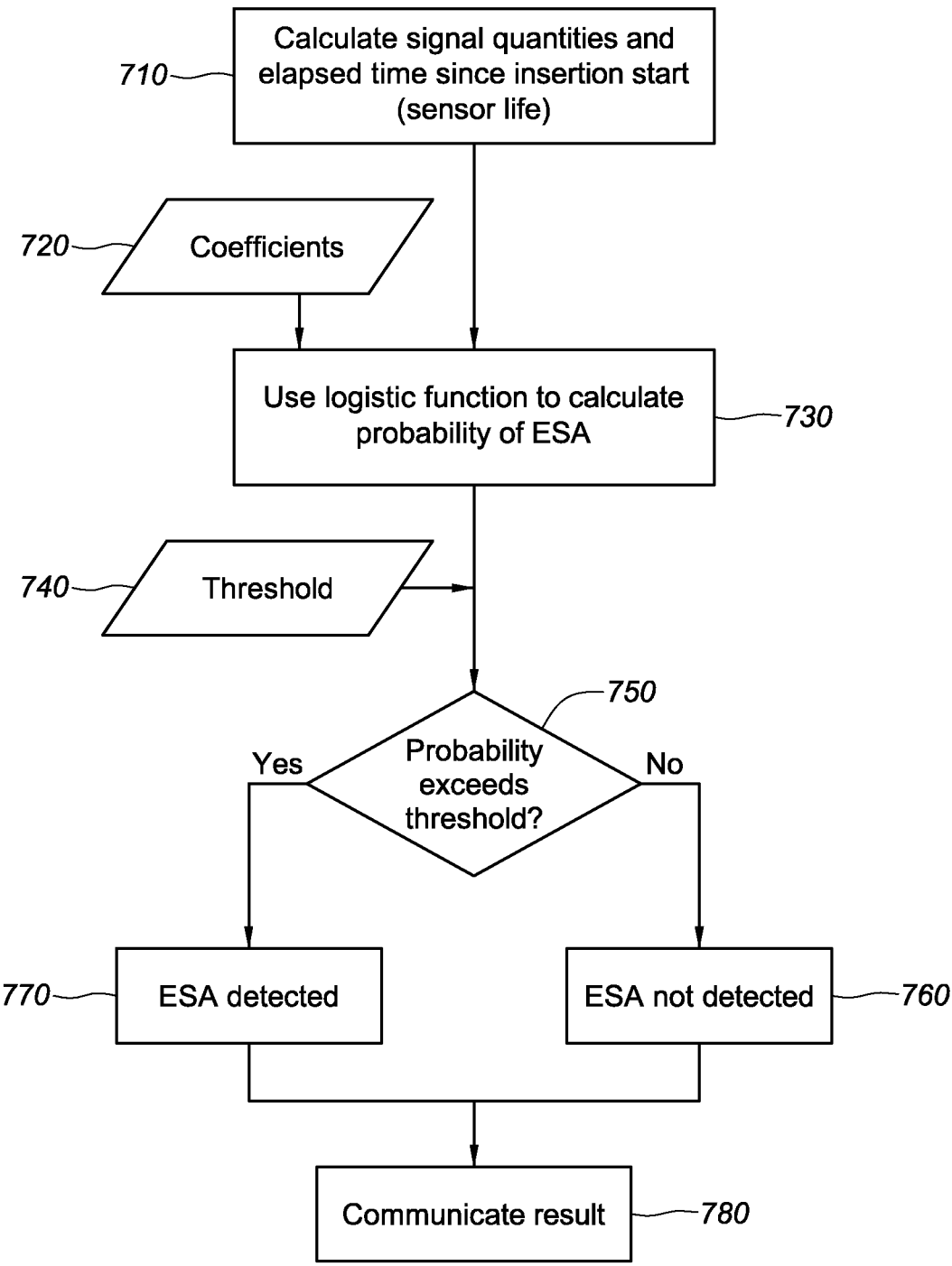
FIG. 7 is a flowchart illustrating real-time detection of sensor current abnormalities described in conjunction with module 1 of FIG. 5 in accordance with one embodiment of the present disclosure.

FIG. 7 is a flowchart illustrating real-time detection of sensor current abnormalities described in conjunction with module 1 of FIG. 5 in accordance with one embodiment of the present disclosure. Referring to FIG. 7, in one embodiment, analyte sensor data for a defined time period is retrieved or selected. With the analyte sensor data, one or more data processing is performed to determine sensor signal characteristics, including, for example, the mean current signal, the least squares slope, a standard deviation, an average elapsed time since the analyte sensor insertion/positioning (or average sensor life), a variance about the least squares slope (710).

Referring to FIG. 7, predetermined coefficients based on the analyte sensor data may be retrieved (720), and applied to the analyte sensor signals to determine or estimate the probability of ESA presence (730). Additionally, further shown in FIG. 7 is a predetermined threshold (740) which in one embodiment may be compared to the determined estimated probability of ESA presence (750). In one aspect, the predetermined threshold may be determined as the minimum probability of ESA presence for declaring such condition, and may be a tradeoff between false alarms (false positives, where the threshold may be easy to exceed) versus missed detections (false negatives, where the threshold is difficult to exceed).

Referring still again to FIG. 7, if it is determined that the estimated probability of ESA presence does not exceed the predetermined threshold (750), then it is determined that ESA is not present—that is, sensor current signal attenuation is not detected (760). On the other hand, if it is determined that estimated probability of ESA presence exceeds the predetermined threshold, it is determined that ESA is present—that is, sensor current signal attenuation is detected (770). In either case, where the ESA presence is determined to be present or not present, such determination is communicated or provided to the subsequent stage in the analysis (780) for further processing.

Figure 8:
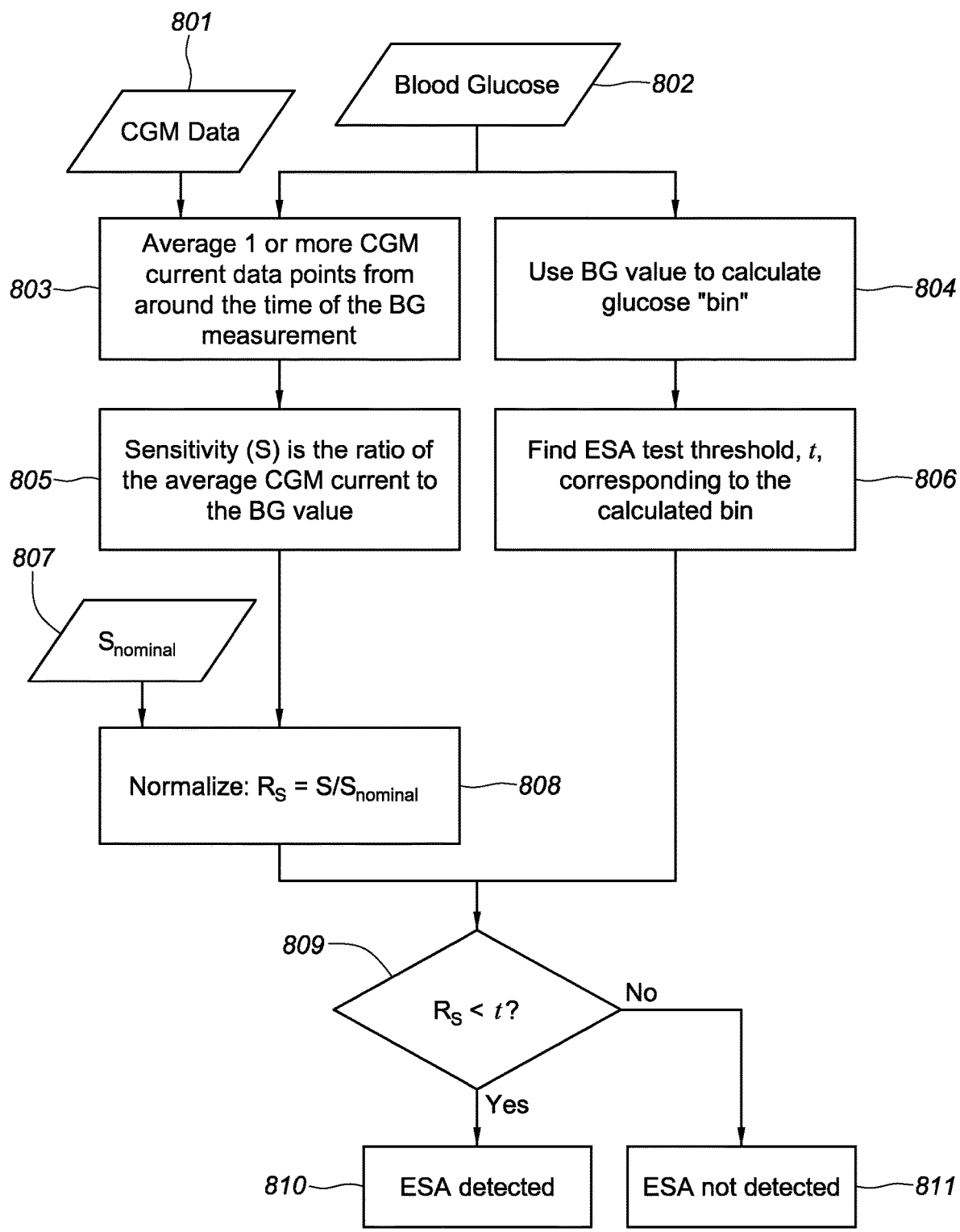
FIG. 8 is a flowchart illustrating verification routine of module 2 in FIG. 5 to confirm or reject the output of module 1 in accordance with one embodiment of the present disclosure.

FIG. 8 is a flowchart illustrating verification routine of module 2 in FIG. 5 to confirm or reject the output of module 1 in accordance with one embodiment of the present disclosure. Referring to FIG. 8, with the continuous glucose data (801) and the capillary blood glucose measurement (802), an average function of one or more continuous glucose sensor current data point at around the same time or approximately contemporaneously with the blood glucose measurement is performed (803). In the case where the sensor current data point is a single value, average function will result in the value itself—therefore averaging routine is unnecessary.

Alternatively, in the case where the sensor data includes more than one data point, for example, 11 data points centered around the time of the blood glucose data point, the average function is performed resulting in an average value associated with the plurality of data points. Thereafter, as shown in FIG. 8, a sensitivity value (S) is determined based on the calculated average value of the sensor data points as described above and the capillary blood glucose measurement (805). For example, the sensitivity value (S) associated with the sensor may be determined as the ratio of the determined average sensor data point value to the blood glucose value.

Referring still to FIG. 8, a nominal sensor sensitivity typically determined at the time of sensor manufacturing (807) is retrieved and applied to the determined sensor sensitivity value (S) to attain a normalized sensitivity ratio Rs (808).

Referring back to FIG. 8, based on the measured or received capillary blood glucose measurement (802), a corresponding glucose bin described above is determined or calculated (804), for example, in one aspect, by applying the function described in equation (5) above. Thereafter, a corresponding ESA test threshold t is determined (806) based on the calculated or determined glucose bin. For example, as described above, each glucose bin (bin1 to bin6), is associated with a respective threshold level t which may, in one aspect, be determined by prior analysis or training.

Referring still again to FIG. 8, with the normalized sensitivity ratio (808) and the calculated bin (806), a comparison is made between the normalized sensitivity ratio and the determined or calculated bin (809). For example, in the case where the comparison establishes the normalized sensitivity ratio (Rs) exceeds the calculated bin t, it is determined that early signal attenuation (ESA) is not present (811). On the other hand, when the normalized sensitivity ratio (Rs) is determined to be less than the calculated bin t, then it is determined that ESA in the sensor signals is present (810).

Figure 9:
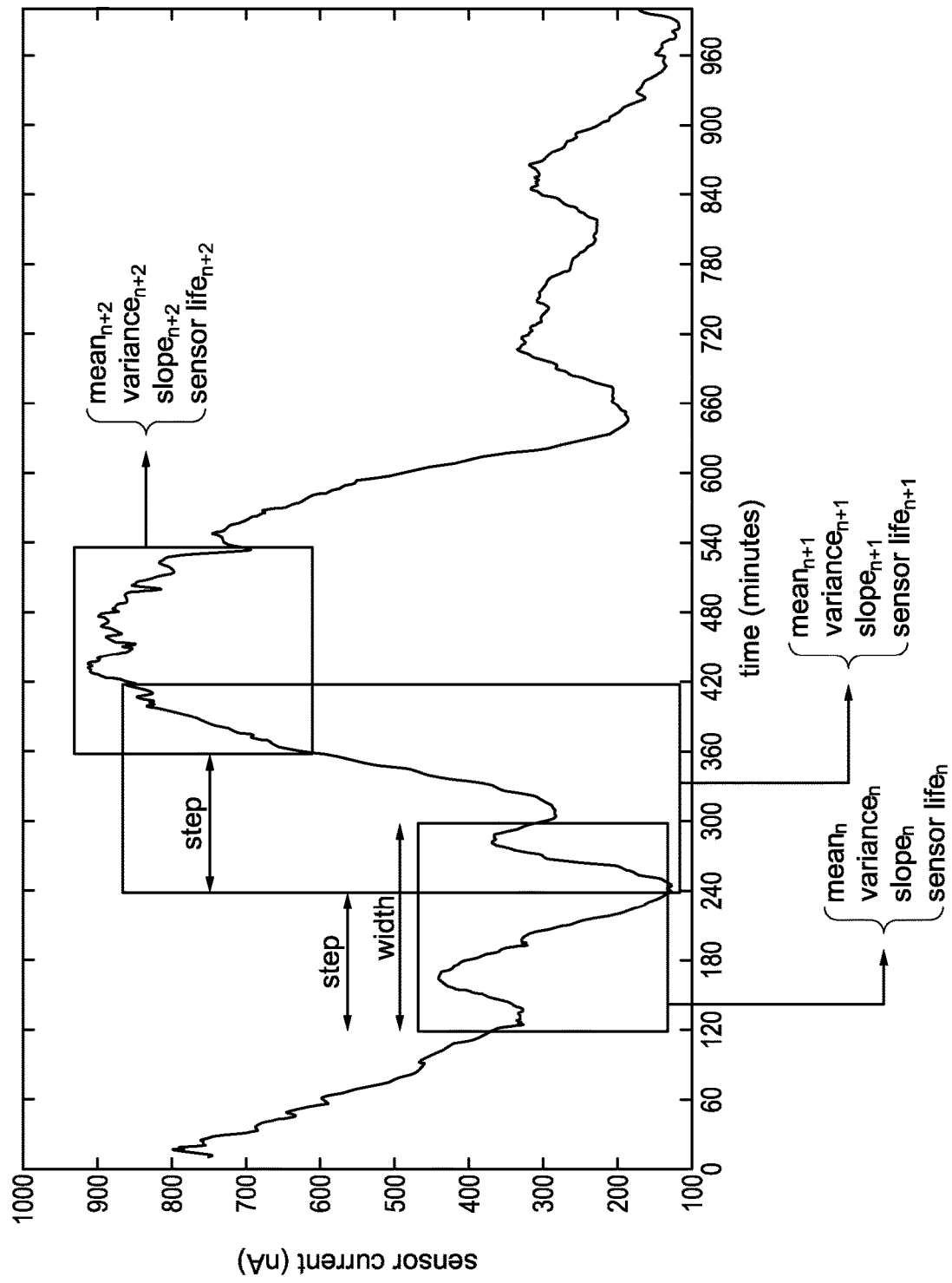
FIG. 9 illustrates a real time current signal characteristics evaluation approach based on a sliding window process of module 1 in FIG. 5 in accordance with one embodiment of the present disclosure.

FIG. 9 illustrates a real time current signal characteristics evaluation approach based on a sliding window process of module 1 in FIG. 5 in accordance with one embodiment of the present disclosure.

FIG. 10 illustrates bootstrap estimation of coefficients for module 1 of FIG. 5 in accordance with one embodiment of the present disclosure. Referring to the Figures, the bootstrap estimation procedure performed to add robustness to the model coefficients may include, in one aspect, a generalized linear model fit applied to a predetermined time period to determine the coefficient vector β. Based on a predefined number of iterations, an empirical probability distribution function of each coefficient may be determined, for example, as shown in FIG. 10, where each selected coefficient corresponds to the mode of the associated distribution.

FIG. 11 illustrates Gaussian kernel estimation of the normalized sensitivity density of module 2 of FIG. 5 in accordance with one embodiment of the present disclosure. Referring to FIG. 11, as described above in conjunction with FIG. 5, in one aspect, kernel density estimation (using Gaussian kernel, for example) may be used to estimate the distribution of the sensitivity ratio Rs in each bin/category described above. The estimation of the distribution in sensitivity ratio Rs in one aspect is shown in FIG. 11, where for each bin/category (including, for example, severe hypoglycemia (bin1), mild hypoglycemia (bin2), low euglycemia (bin3), high euglycemia (bin4), mild hyperglycemia (bins), and high hyperglycemia (bin6)), the corresponding chart illustrates the associated distribution where ESA presence is detected as compared to the distribution where no ESA presence is detected.

Figure 12:
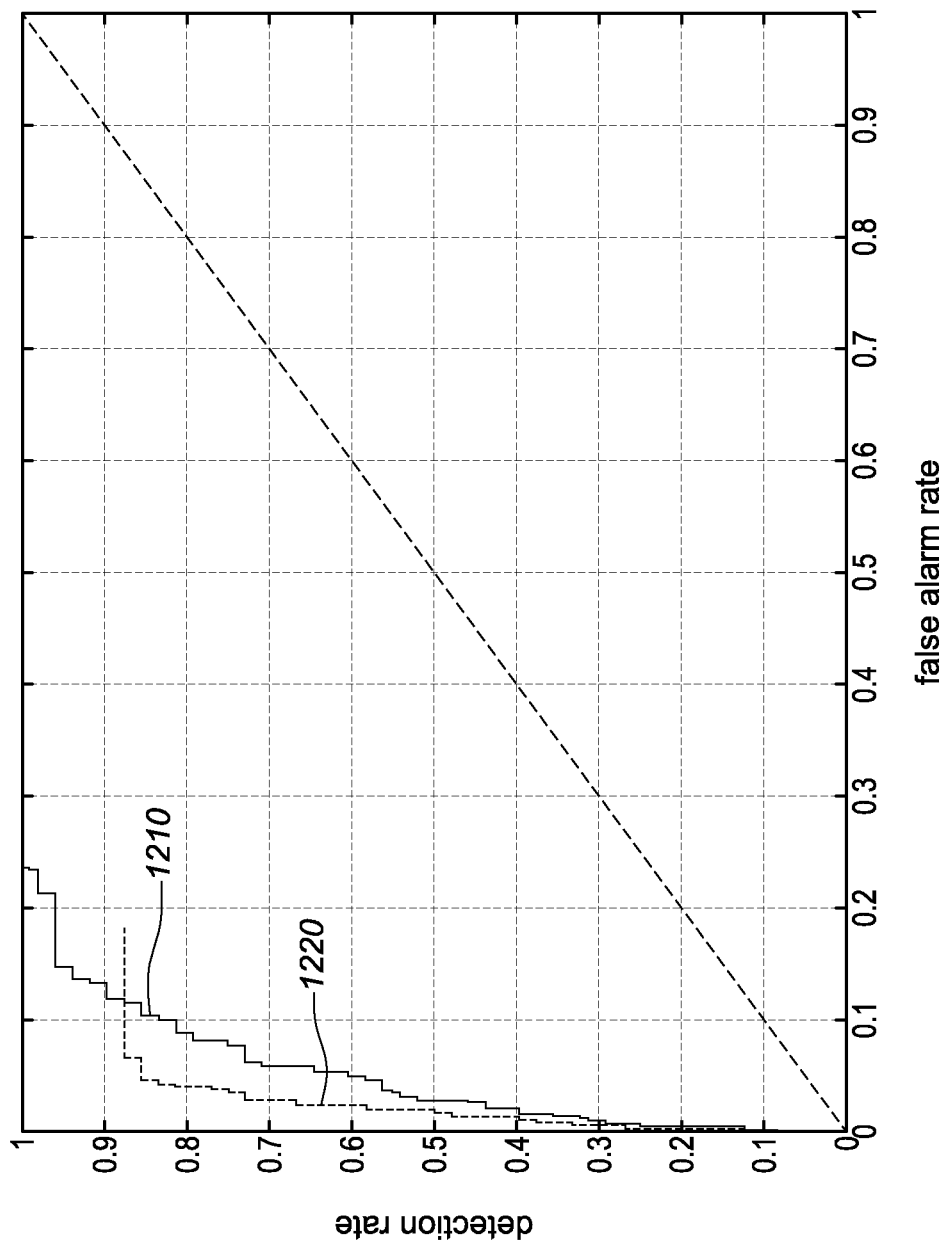
FIG. 12 illustrates output curve of the first module compared with the output curve of the combined first and second modules of FIG. 5, based on a predetermined test data set and detection threshold of FIG. 7 in accordance with embodiment of the present disclosure.

FIG. 12 illustrates a comparison of rate of false alarms (false positives) and sensitivity decline detection rate in accordance with the embodiment of the present disclosure. That is, FIG. 12 represents the relation between ESA detection rate and false alarm rate. In one aspect, curve 1210 illustrates the output results of the first module 510 in the sensitivity decline detector 500 (FIG. 5) based on the logistic regression classifier, while curve 1220 illustrates the combined output of the first module 510 and the second module 520 of the sensitivity decline detector 500 (FIG. 5) based, for example, on a logistic rule classifier prompting a blood glucose measurement in the case of ESA presence probability exceeding a predetermined threshold level. In one embodiment, based on a threshold level of 0.416 determining the ESA presence probability, the rate of ESA detection is approximately 87.5% and a false alarm rate is approximately 6.5%.

In the manner described above, in accordance with the various embodiments of the present disclosure, real time detection of ESA or night time dropouts of analyte sensor sensitivities are provided. For example, an analyte sensor with lower than normal sensitivity may report blood glucose values lower than the actual values, thus potentially underestimating hyperglycemia, and triggering false hypoglycemia alarms. Moreover, since the relationship between the sensor current level and the blood glucose level is estimated using a reference blood glucose value (for example, calibration points), if such calibration is performed during a low sensitivity period, once the period comes to an end, all glucose measurements will be positively biased, thus potentially masking hypoglycemia episodes. Accordingly, the occurrence of errors in the relation between the current signal output of the analyte sensor and the corresponding blood glucose level may be monitored and detected in real time such that the patients may be provided with the ability to take corrective actions.

Indeed, real time detection of variations in the glucose levels in patients using monitoring devices such as analyte monitoring devices provide temporal dimension of glucose level fluctuations which provide the ability to tightly control glycemic variation to control diabetic conditions. More specifically, in accordance with the various embodiments of the present disclosure, the analyte monitoring systems may be configured to provide warnings about low glucose levels in real time in particular, when the patient may not be suspecting hypoglycemia or impending hypoglycemia, and thus provide the ability to help patients avoid life-threatening situations and self-treat during hypoglycemic attacks.

Accordingly, in one aspect of the present disclosure, the detection of episodes of low sensor sensitivity includes a first module which may be configured to execute a real-time detection algorithm based on analyte sensor current signal characteristics, and further, a second module which may be configured to perform a statistical analysis based on a single blood glucose measurement to confirm or reject the initial detection of the sensor sensitivity decline performed by the first module. In this manner, in one aspect of the present disclosure, accurate detection of ESA episodes or night time dropouts or declines in sensor current signal levels may be provided with minimal false alarms.

Accordingly, a computer implemented method in one aspect includes receiving a plurality of analyte sensor related signals, determining a probability of signal attenuation associated with the received plurality of analyte sensor related signals, verifying the presence of signal attenuation when the determined probability exceeds a predetermined threshold level, and generating a first output signal associated with the verification of the presence of signal attenuation.

Further, determining the probability of signal attenuation may include determining one or more characteristics associated with the received plurality of analyte sensor related signals, and applying a predetermined coefficient to the plurality of analyte sensor related signals.

In another aspect, the determined one or more characteristics may include one or more mean value associated with the analyte sensor related signals, the least square slope associated with the analyte sensor related signals, a standard deviation associated with the analyte sensor related signals, an average elapsed time from positioning the analyte sensor, or a variance about a least squares slope associated with the analyte sensor related signals.

Also, in still another aspect, the predetermined threshold level may be user defined or defined by a system expert.

In still another aspect, when the determined probability does not exceed the predetermined threshold level, the method may further include generating a second output signal associated with absence of signal attenuation condition.

Additionally, in yet a further aspect, verifying the presence of signal attenuation may include selecting a signal attenuation threshold level, determining a sensitivity level associated with the analyte related sensor signals, and confirming the presence of signal attenuation based at least in part on a comparison of the determined sensitivity level and the selected signal attenuation threshold level, where the signal attenuation threshold level may be associated with a blood glucose measurement.

Also, the blood glucose measurement may in another aspect include a capillary blood glucose sampling.

In yet still another aspect, the sensitivity level associated with the analyte related sensor may include a ratio of nominal sensitivity associated with the analyte related sensor signals and the sensitivity value associated with the analyte related sensor signals, where the sensitivity value may be determined as a ratio of the average of the analyte related sensor signals and a blood glucose measurement.

Moreover, confirming the presence of signal attenuation in another aspect may include determining that the sensitivity level is less than the selected signal attenuation threshold level, which in one aspect, may be determined by a system expert.

An apparatus in accordance with another aspect of the present disclosure includes a data storage unit, and a processing unit operatively coupled to the data storage unit configured to receive a plurality of analyte sensor related signals, determine a probability of signal attenuation associated with the received plurality of analyte sensor related signals, verify the presence of signal attenuation when the determined probability exceeds a predetermined threshold level, and generate a first output signal associated with the verification of the presence of signal attenuation.

The processing unit may be configured to determine the probability of signal attenuation and is configured to determine one or more characteristics associated with the received plurality of analyte sensor related signals, and to apply a predetermined coefficient to the plurality of analyte sensor related signals.

The determined one or more characteristics may include one or more mean value associated with the analyte sensor related signals, the least square slope associated with the analyte sensor related signals, a standard deviation associated with the analyte sensor related signals, an average elapsed time from positioning the analyte sensor, or a variance about a least squares slope associated with the analyte sensor related signals, where the predetermined threshold level may be user defined, or defined by a system expert.

When the determined probability does not exceed the predetermined threshold level, the processing unit may be further configured to generate a second output signal associated with absence of signal attenuation condition.

In still another aspect, the processing unit may be further configured to select a signal attenuation threshold level, determine a sensitivity level associated with the analyte related sensor signals, and confirm the presence of signal attenuation based at least in part on a comparison of the determined sensitivity level and the selected signal attenuation threshold level.

The signal attenuation threshold level may be associated with a blood glucose measurement.

The blood glucose measurement may include a capillary blood glucose sampling.

The sensitivity level associated with the analyte related sensor may include a ratio of nominal sensitivity associated with the analyte related sensor signals and the sensitivity value associated with the analyte related sensor signals, where the sensitivity value may be determined as a ratio of the average of the analyte related sensor signals and a blood glucose measurement.

The processing unit may be further configured to determine that the sensitivity level is less than the selected signal attenuation threshold level, which may be, in one aspect determined by a system expert.

In still another aspect, the apparatus may include a user output unit operatively coupled to the processing unit to display the first output signal.

A system for detecting signal attenuation in a glucose sensor in still another aspect of the present disclosure includes an analyte sensor for transcutaneous positioning through a skin layer of a subject, a data processing device operatively coupled to the analyte sensor to periodically receive a signal associated with the analyte sensor, the data processing device configured to determine a probability of the early signal attenuation (ESA), and to verify the presence of early signal attenuation based on one or more predetermined criteria.

The data processing device may include a user interface to output one or more signals associated with the presence or absence of early signal attenuation associated with the analyte sensor.

Various other modifications and alterations in the structure and method of operation of this disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. It is intended that the following claims define the scope of the present disclosure and that structures and methods within the scope of these claims and their equivalents be covered thereby.

What is claimed is:
1. A system, comprising:
a sensor comprising:
a proximal portion configured to be positioned above a user's skin and to be electrically coupled with a processing unit and
a distal portion configured to be transcutaneously positioned through a user's skin and in contact with a biological fluid of the user, wherein the distal portion is configured to detect a lactate level in the biological fluid;
a data storage unit; and
the processing unit operatively coupled to the data storage unit and operatively coupled to the proximal portion, the processing unit programmed to:
perform a sliding window analysis on a set of lactate sensor data, wherein the set of lactate sensor data is taken over a first time period after initialization of a sensor, and wherein in performance of the sliding window analysis, the processing unit is programmed to:
extract a first sensor data characteristic for a first window of the set of lactate sensor data, wherein the first window starts at a first start time, ends at a first end time, and has a first duration less than the first time period; and
extract a second sensor data characteristic for a second window of the set of lactate sensor data, wherein the second window starts at a second start time after the first start time, ends at a second end time after the first end time, and has a second duration less than the first time period; and
determine a probable existence of a sensor current variance relative to a predetermined threshold based on the first and second sensor data characteristics.

2. The system of claim 1, wherein the sensor current variance relative to a predetermined threshold comprise signal attenuation associated with a decline in lactate sensor sensitivity.

3. The system of claim 1, wherein the second start time is before the first end time such that the first and second windows overlap.

4. The system of claim 1, wherein the second start time is at the first end time.

5. The system of claim 1, wherein the first and second windows are non-overlapping.

6. The system of claim 1, wherein the first and second durations are the same.

7. The system of claim 1, wherein the first sensor data characteristic is a mean value or a variance value.

8. The system of claim 1, wherein the first sensor data characteristic is an average slope of a sensor signal.

9. The system of claim 1, wherein the first sensor data characteristic is an average sensor life or a time elapsed since insertion of the sensor.

10. The system of claim 1, wherein the first time period includes a time in the first twelve to twenty four hours after insertion of the sensor.

11. The system of claim 1, wherein the lactate sensor data comprises glucose sensor data.

12. The system of claim 1, wherein the lactate sensor data comprises lactate sensor data.

13. The system of claim 1, wherein sensor current characteristics comprise a mean current and a current variance.

14. A system, comprising:
a sensor comprising:
a proximal portion configured to be positioned above a user's skin and to be electrically coupled with a processing unit and
a distal portion configured to be transcutaneously positioned through a user's skin and in contact with a biological fluid of the user, wherein the distal portion is configured to detect a lactate level in the biological fluid, the distal portion comprising a working electrode, a counter electrode, and a reference electrode;
a data storage unit; and
the processing unit operatively coupled to the data storage unit and operatively coupled to the proximal portion, the processing unit programmed to:
perform a sliding window analysis on a set of lactate sensor data, wherein the set of lactate sensor data is taken over a first time period after initialization of a sensor, and wherein in performance of the sliding window analysis, the processing unit is programmed to:
extract a first sensor data characteristic for a first window of the set of lactate sensor data, wherein the first window starts at a first start time, ends at a first end time, and has a first duration less than the first time period; and
extract a second sensor data characteristic for a second window of the set of lactate sensor data, wherein the second window starts at a second start time after the first start time, ends at a second end time after the first end time, and has a second duration less than the first time period; and
determine a probable existence of a sensor current variance relative to a predetermined threshold based on the first and second sensor data characteristics.

15. The system of claim 14, wherein sensor current characteristics comprise a mean current and a current variance.

* * * * *